(12) United States Patent
Mudd et al.

(10) Patent No.: US 11,306,123 B2
(45) Date of Patent: Apr. 19, 2022

(54) HETEROTANDEM BICYCLIC PEPTIDE COMPLEX

(71) Applicant: BicycleTx Limited, Cambridge (GB)

(72) Inventors: Gemma Mudd, Cambridge (GB); Punit Upadhyaya, Lexington, MA (US); Kevin McDonnell, Lexington, MA (US); Johanna Lahdenranta, Lexington, MA (US)

(73) Assignee: BICYCLETX LIMITED, Cambridge (GB)

( * ) Notice: Subject to any disclaimer, the term of this patent is extended or adjusted under 35 U.S.C. 154(b) by 0 days.

(21) Appl. No.: 16/941,614

(22) Filed: Jul. 29, 2020

(65) Prior Publication Data

US 2021/0040154 A1   Feb. 11, 2021

Related U.S. Application Data

(60) Provisional application No. 63/024,715, filed on May 14, 2020, provisional application No. 63/022,667, filed on May 11, 2020, provisional application No. 62/931,442, filed on Nov. 6, 2019, provisional application No. 62/910,088, filed on Oct. 3, 2019, provisional application No. 62/880,191, filed on Jul. 30, 2019.

(51) Int. Cl.
| | | |
|---|---|---|
| *C07K 7/08* | (2006.01) | |
| *A61K 38/00* | (2006.01) | |
| *A61P 35/00* | (2006.01) | |
| *A61K 9/00* | (2006.01) | |
| *A61K 38/12* | (2006.01) | |

(52) U.S. Cl.
CPC .............. *C07K 7/08* (2013.01); *A61K 9/0019* (2013.01); *A61K 38/12* (2013.01); *A61P 35/00* (2018.01); *A61K 38/00* (2013.01)

(58) Field of Classification Search
CPC .................................. C07K 7/08; A61K 38/00
See application file for complete search history.

(56) References Cited

U.S. PATENT DOCUMENTS

| | | | |
|---|---|---|---|
| 10,875,894 B2 | 12/2020 | Chen et al. | |
| 10,919,937 B2 | 2/2021 | Beswick et al. | |
| 2019/0263866 A1* | 8/2019 | Chen | A61K 47/60 |
| 2019/0307836 A1 | 10/2019 | Keen et al. | |
| 2019/0389906 A1 | 12/2019 | Beswick et al. | |
| 2020/0255477 A1 | 8/2020 | Chen et al. | |
| 2020/0338203 A1 | 10/2020 | Chen et al. | |
| 2020/0354406 A1 | 11/2020 | Stephen et al. | |
| 2021/0069287 A1* | 3/2021 | Mudd | A61K 47/641 |
| 2021/0101932 A1 | 4/2021 | Chen et al. | |
| 2021/0101933 A1 | 4/2021 | Chen et al. | |
| 2021/0101937 A1 | 4/2021 | Mudd et al. | |
| 2021/0147484 A1 | 5/2021 | Beswick et al. | |
| 2021/0299210 A2* | 9/2021 | Keen | C07K 14/001 |

FOREIGN PATENT DOCUMENTS

| | | |
|---|---|---|
| WO | WO-2004/077062 A2 | 9/2004 |
| WO | WO-2010/089115 A1 | 8/2010 |
| WO | WO-2012/057624 A1 | 5/2012 |
| WO | WO-2016/067035 A1 | 5/2016 |
| WO | WO-2017/173408 A1 | 10/2017 |
| WO | WO-2017/182672 A1 | 10/2017 |
| WO | WO-2017/191460 A1 | 11/2017 |
| WO | WO-2018/156740 A1 | 8/2018 |
| WO | WO-2019/025811 A | 2/2019 |
| WO | WO-2019/122861 A1 | 6/2019 |
| WO | WO-2019/122863 A1 | 6/2019 |
| WO | WO-2019/162682 A1 | 8/2019 |
| WO | WO-2019/193328 A1 | 10/2019 |
| WO | WO-2019/243313 A1 | 12/2019 |
| WO | WO-2019/243832 A1 | 12/2019 |
| WO | WO-2019/243833 A1 | 12/2019 |
| WO | WO-2020/084305 A1 | 4/2020 |
| WO | WO-2020/128526 A1 | 6/2020 |
| WO | WO-2020/201753 A1 | 10/2020 |
| WO | WO-2020/225577 A1 | 11/2020 |
| WO | WO-2021/019243 A1 | 2/2021 |
| WO | WO-2021/064428 A1 | 4/2021 |

OTHER PUBLICATIONS

Bicycle Therapeutics, Press Release—MarketWatch.com, Apr. 2018.
Chen et al., "Peptide Ligands Stabilized by Small Molecules," Angew. Chem. Int. Ed., 2014, vol. 53, pp. 1602-1606.
Loktev et al., "Multicyclic Peptides as Scaffolds for the Development of Tumor Targeting Agents," Current Medicinal Chemistry, 2017, vol. 24, pp. 2141-2155.
Morrison, "Chemical Strategies for Bicyclic Peptide Formation," Univ. of Leeds, Sep. 2015, pp. 1-60.
Mulder et al., "Scaffold Optimization in Discontinuous Epitope Containing Protein Mimics of gp120 Using Smart Libraries," Org. Biomol. Chem. 2013, vol. 11, pp. 2676-2684.
Pickens et al., "Practical Considerations, Challenges and Limitations of Bioconjugation via Azide-Alkyne Cycloaddition," Bioconjugate Chem., 2018, vol. 29, pp. 686-701.
Rhodes et al., Chemistry—A European Journal, vol. 23, No. 52, Sep. 2017, pp. 12690-12703.

(Continued)

*Primary Examiner* — Amber D Steele

(74) *Attorney, Agent, or Firm* — Dechert LLP; Andrea L.C. Reid; Gang Wang

(57) ABSTRACT

The present invention relates to a heterotandem bicyclic peptide complex which comprises a first peptide ligand, which binds to Nectin-4, conjugated via a linker to two second peptide ligands, which bind to CD137. The invention also relates to the use of said heterotandem bicyclic peptide complex in preventing, suppressing or treating cancer.

19 Claims, 13 Drawing Sheets

Specification includes a Sequence Listing.

(56) References Cited

OTHER PUBLICATIONS

Smeenk et al., "Reconstructing the Discontinuous and Conformational ß1/ß3-Loop Binding Site on hFSH/hCG by Using Highly Constrained Multicyclic Peptides," ChemBioChem 2015, vol. 16, pp. 91-99.
Upadhyaya, "Activation of CD137 Using Multivalent and Tumour Targeted Bicyclic Peptides," XP055669343, URL:https://www.bicycletherapeutics.com/wp-content/uploads/PU_2019-Peptide-Congress_publication.pdf, Peptide Congress, Apr. 25, 2019, 25 Pages.
PCT International Search Report and Written Opinion for PCT Application No. PCT/GB2020/051827, mailed by the European Patent Office dated Nov. 3, 2020, 8 Pages.

\* cited by examiner

A

B

A

B

FIGURE 2 (ctd)

A

B

A

B

C

D

E

FIGURE 10 (ctd)

A

B

C

HETEROTANDEM BICYCLIC PEPTIDE COMPLEX

FIELD OF THE INVENTION

The present invention relates to a heterotandem bicyclic peptide complex which comprises a first peptide ligand, which binds to Nectin-4, conjugated via a linker to two second peptide ligands, which bind to CD137. The invention also relates to the use of said heterotandem bicyclic peptide complex in preventing, suppressing or treating cancer.

BACKGROUND OF THE INVENTION

Cyclic peptides can bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296 (5565), 151-5) or the cyclic peptide inhibitor upain-1 binding to urokinase-type plasminogen activator (603 $Å^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem).

Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) are disclosed in WO 2019/122860 and WO 2019/122863.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a heterotandem bicyclic peptide complex comprising:
(a) a first peptide ligand which binds to Nectin-4 and which has the sequence C$_i$P[1Nal][dD]C$_{ii}$M[HArg]DWSTP[HyP]WC$_{iii}$ (SEQ ID NO: 1; BCY8116); conjugated via an N-(acid-PEG$_3$)-N-bis(PEG$_3$-azide) linker to
(b) two second peptide ligands which bind to CD137 both of which have the sequence Ac-C$_i$[tBuAla]PE[D-Lys(PYA)]PYC$_{ii}$FADPY[Nle]C$_{iii}$-A (SEQ ID NO: 2; BCY8928); wherein each of said peptide ligands comprise a polypeptide comprising three reactive cysteine groups (C$_i$, C$_{ii}$ and C$_{iii}$), separated by two loop sequences, and a molecular scaffold which is 1,1',1"-(1,3,5-triazinane-1,3,5-triyl)triprop-2-en-1-one (TATA) and which forms covalent bonds with the reactive cysteine groups of the polypeptide such that two polypeptide loops are formed on the molecular scaffold; wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

According to a further aspect of the invention, there is provided a pharmaceutical composition comprising a heterotandem bicyclic peptide complex as defined herein in combination with one or more pharmaceutically acceptable excipients.

According to a further aspect of the invention, there is provided a heterotandem bicyclic peptide complex as defined herein for use in preventing, suppressing or treating cancer.

BRIEF DESCRIPTION OF THE FIGURES

FIG. 2C represents a summary of EC50 (nM) of BCY11863 in the cytokine secretion assay with multiple human PBMC donors and tumor cell lines.

DETAILED DESCRIPTION OF THE INVENTION

According to a first aspect of the invention, there is provided a heterotandem bicyclic peptide complex comprising:
(a) a first peptide ligand which binds to Nectin-4 and which has the sequence $C_iP[1Nal][dD]C_{ii}M[HArg]DWSTP[HyP]WC_{iii}$ (SEQ ID NO: 1; BCY8116); conjugated via an N-(acid-PEG$_3$)-N-bis(PEG$_3$-azide) linker to
(b) two second peptide ligands which bind to CD137 both of which have the sequence Ac-$C_i$[tBuAla]PE[D-Lys(PYA)]PY$C_{ii}$FADPY[Nle]$C_{iii}$-A (SEQ ID NO: 2; BCY8928); wherein each of said peptide ligands comprise a polypeptide comprising three reactive cysteine groups ($C_i$, $C_{ii}$ and $C_{iii}$), separated by two loop sequences, and a molecular scaffold which is 1,1',1"-(1,3,5-triazinane-1,3,5-triyl)triprop-2-en-1-one (TATA) and which forms covalent bonds with the reactive cysteine groups of the polypeptide such that two polypeptide loops are formed on the molecular scaffold;
wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

References herein to a N-(acid-PEG$_3$)-N-bis(PEG$_3$-azide) linker include:

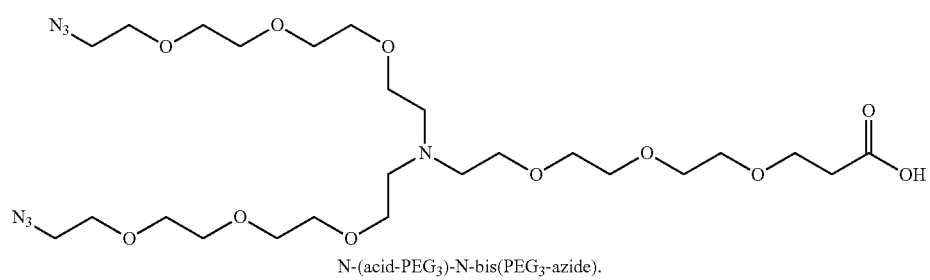 [SMILES: [N-]=[N+]=NCCOCCOCCOCCN(CCOCCOCCOCCN=[N+]=[N-])CCOCCOCCOCCC(=O)O]

N-(acid-PEG$_3$)-N-bis(PEG$_3$-azide).

In one embodiment, the heterotandem bicyclic peptide complex is BCY11863:
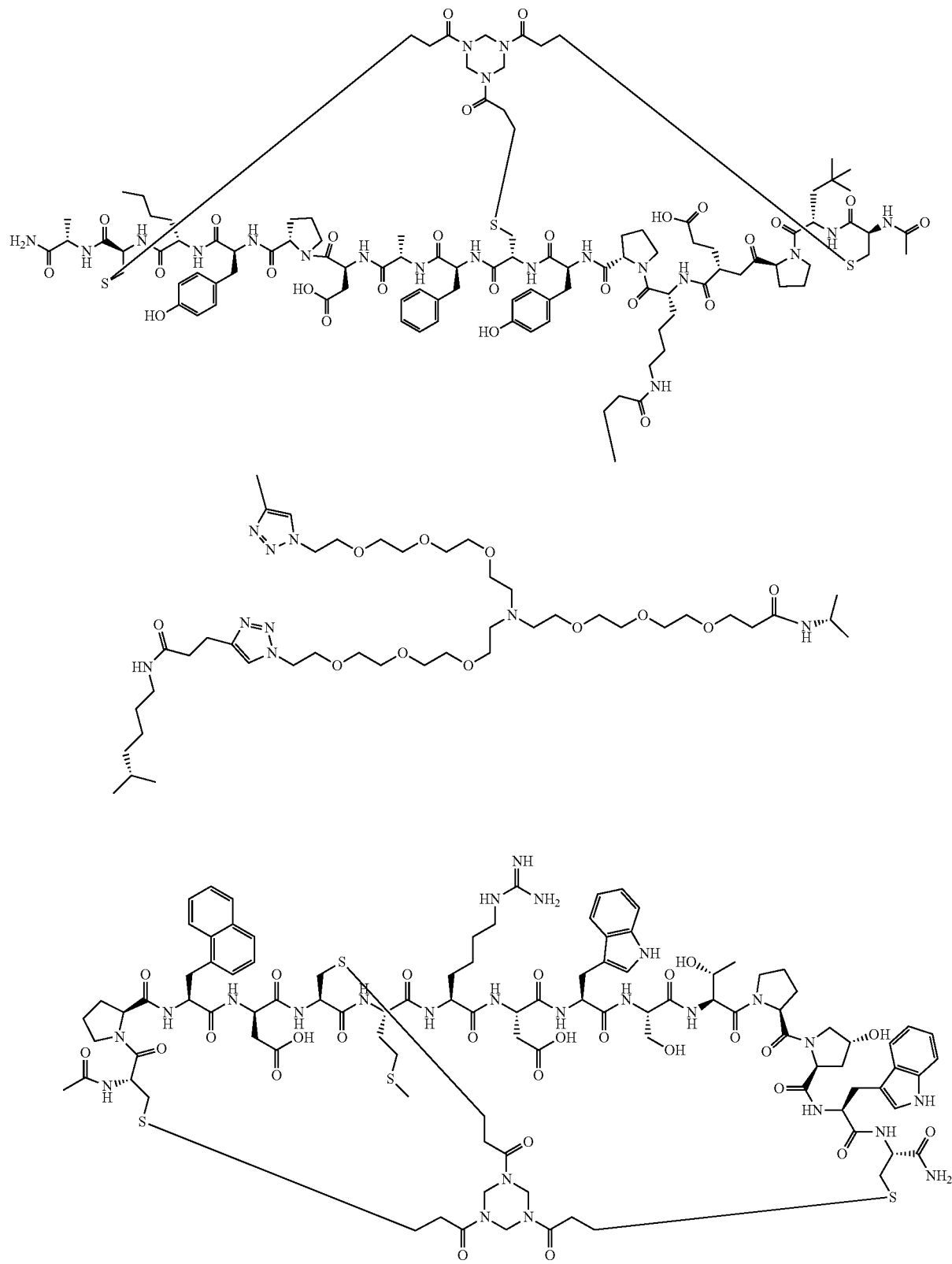

-continued

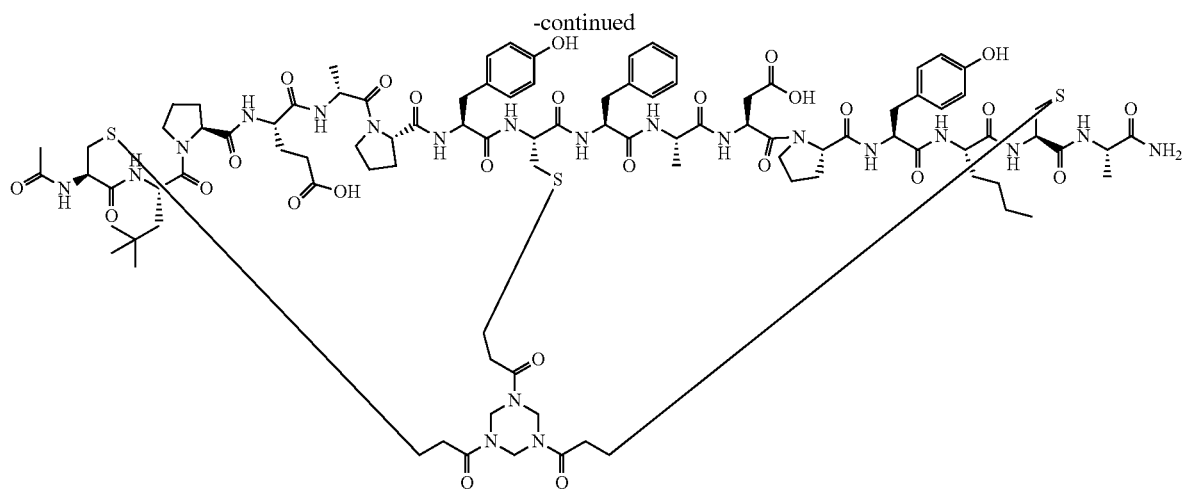

Full details of BCY11863 are shown in Table A below:

TABLE A

Composition of BCY11863

| Complex No. | Nectin-4 BCY No. | Attachment Point | Linker | CD137 BCY Nos. | Attachment Point |
|---|---|---|---|---|---|
| BCY11863 | BCY8116 | N-terminus | N-(acid-PEG3)-N-bis(PEG3-azide) | BCY8928, BCY8928 | dLys (PYA)4 |

Figure 1:
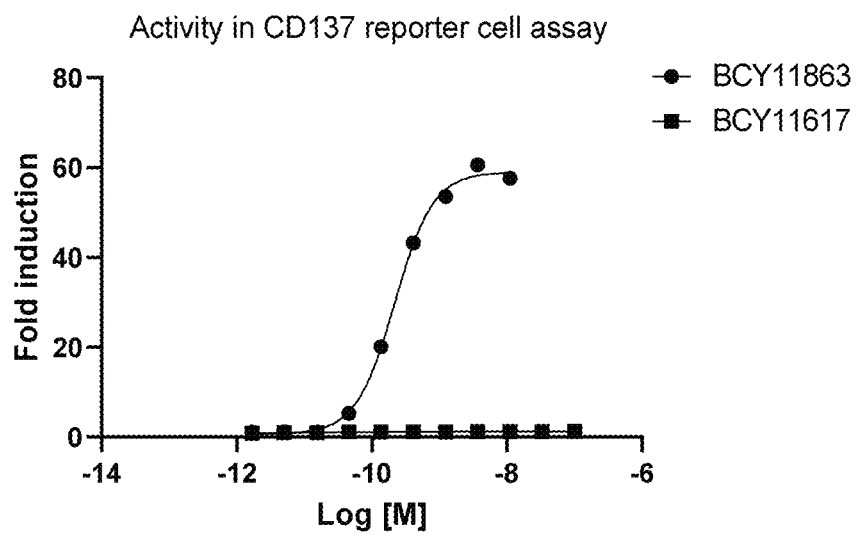
FIG. 1: (A) Analysis of the Nectin-4/CD137 heterotandem bicyclic peptide complex in the Promega CD137 luciferase reporter assay in the presence of Nectin-4 expressing H292 cells. BCY11617 is a heterotandem bicyclic peptide complex that binds to Nectin-4 with the same affinity as BCY11863 but that does not bind to CD137. (B) Summary of EC50 (nM) of BCY11863 in the Promega CD137 luciferase reporter assay in coculture with different cell lines that express Nectin-4 endogenously or are engineered to overexpress Nectin-4.
Figure 1:
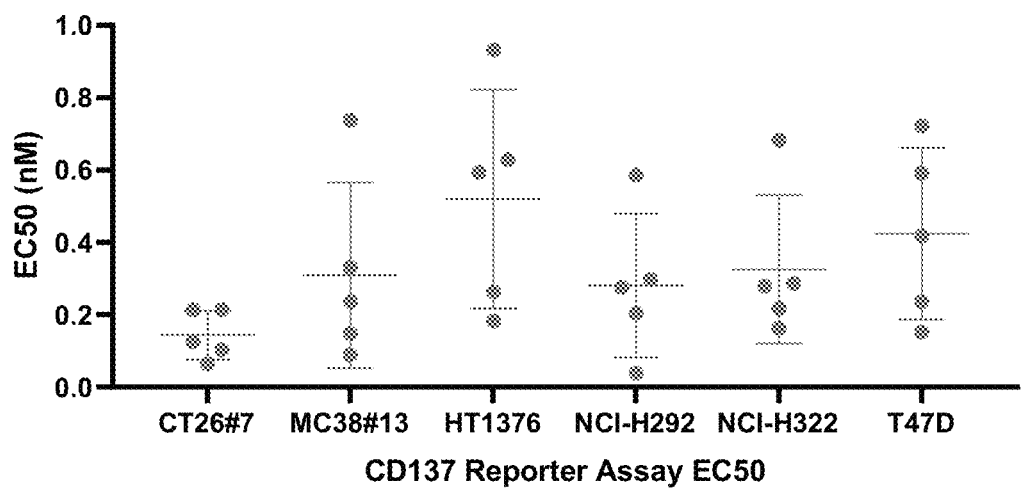
Figure 2:
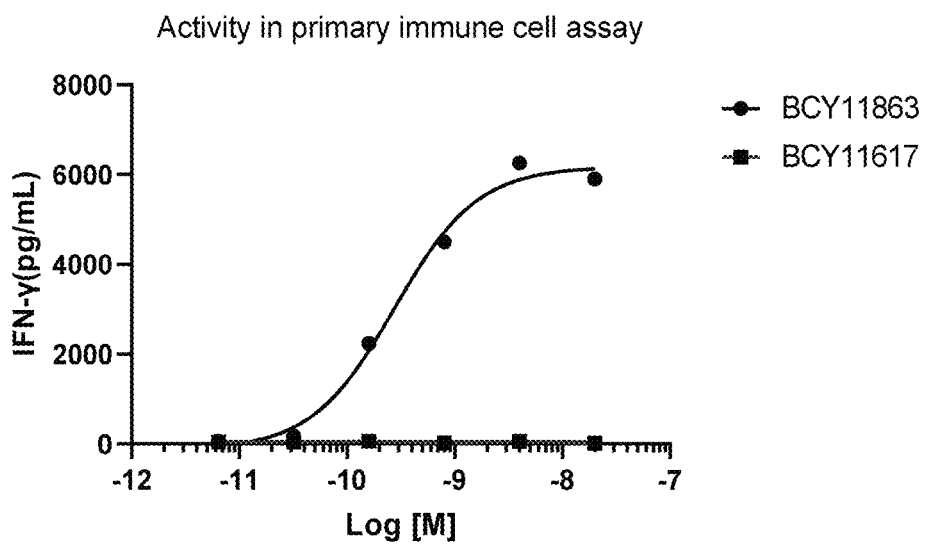
FIG. 2: Nectin-4/CD137 heterotandem bicyclic peptide complexes induce IFN-γ (FIG. 2A) and IL-2 (FIG. 2B) cytokine secretion in a PBMC-4T1 co-culture assay. 4T1 cells were engineered to express Nectin-4. BCY11617 is a heterotandem bicyclic peptide complex that binds to Nectin-4 with the same affinity as BCY11863 but does not bind to CD137.
Figure 2:
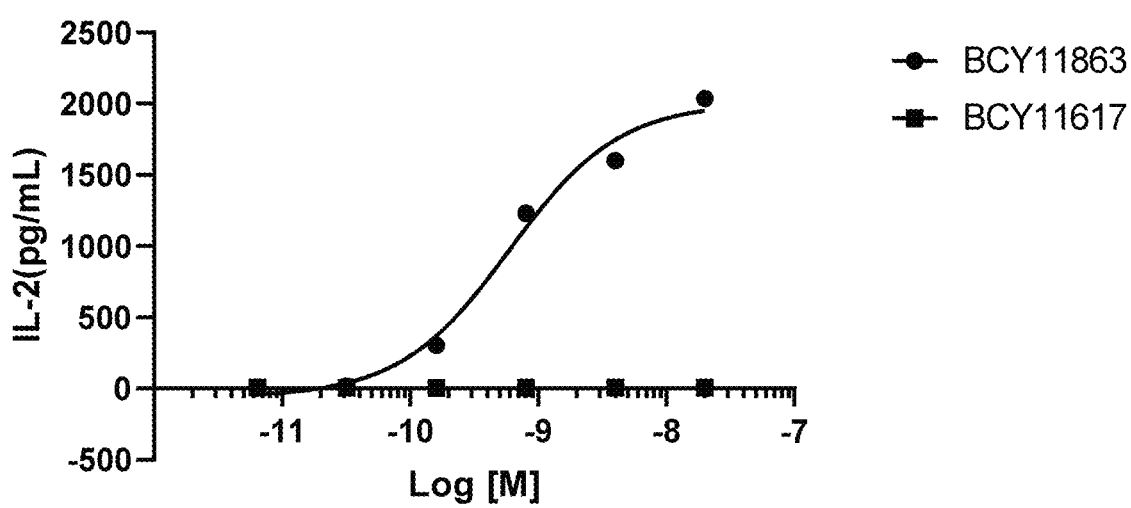
Figure 4:
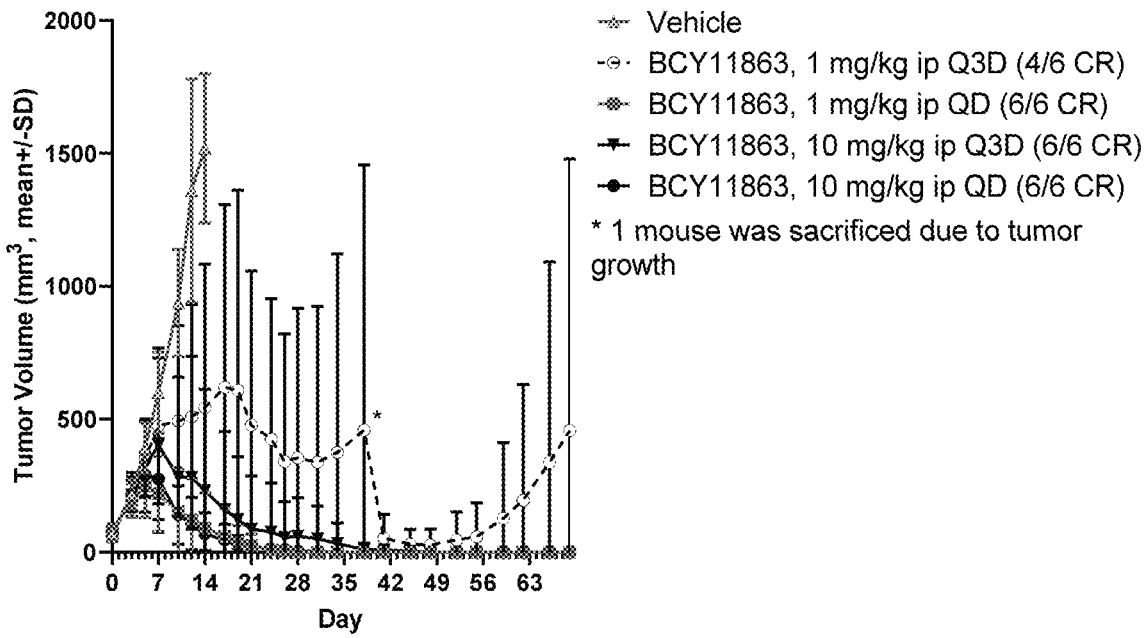
FIG. 4: Anti-tumor activity of BCY11863 in a syngeneic mouse Nectin-4 overexpressing MC38 tumor model (MC38#13). Tumor volumes during and after BCY11863 treatment. Number of complete responder (CR) mice on D69 are indicated in parentheses. QD: daily dosing; Q3D: every three days dosing; ip: intraperitoneal administration.
Figure 5:
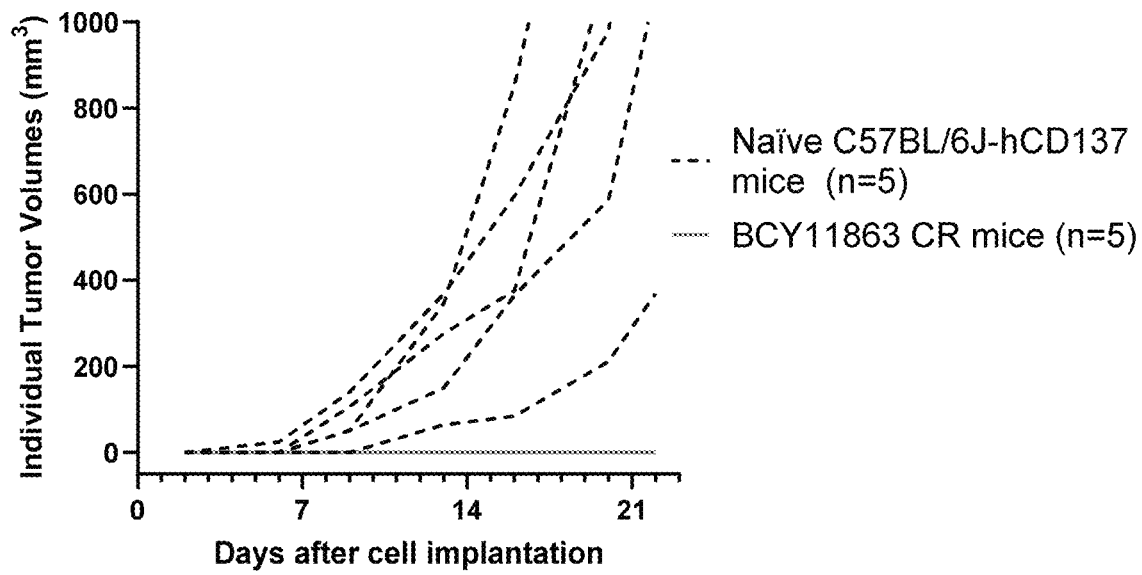
FIG. 5: BCY11863 treatment leads to an immunogenic memory to Nectin-4 overexpressing MC38 tumor cells (MC38#13). Tumor volumes are shown after inoculation to naïve C57BL/6J-hCD137 mice or mice that had complete responses (CR) to BCY11863. Note that none of the CR mice developed tumors by the end of the observation period (22 days).
Figure 6:
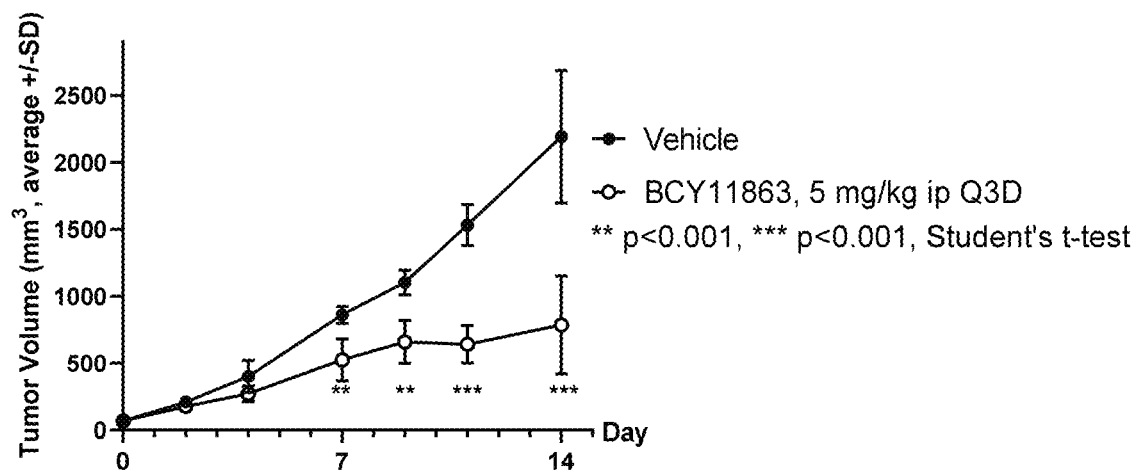
FIG. 6: BCY11863 demonstrates anti-tumor activity in a mouse syngeneic Nectin-4 overexpressing CT26 tumor model (CT26#7). Tumor volumes during BCY11863 treatment. Q3D: every three days dosing; ip: intraperitoneal administration.
Figure 7:
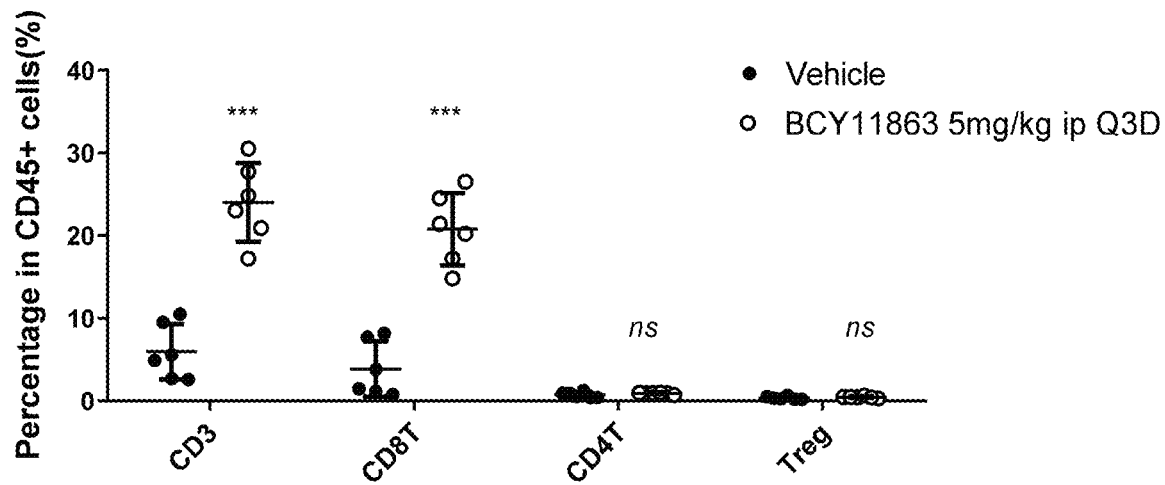
FIG. 7: Total T cells and CD8+ T cells increase in CT26#7 tumor tissue 1 h after the last (6th) Q3D dose of BCY11863. Analysis of (A) total T cells, CD8+ T cells, CD4+ T cells, Tregs and (B) CD8+ T cell/Treg-ratio in CT26#7 tumor tissue 1 h after last Q3D dose of BCY11863.
Figure 7:
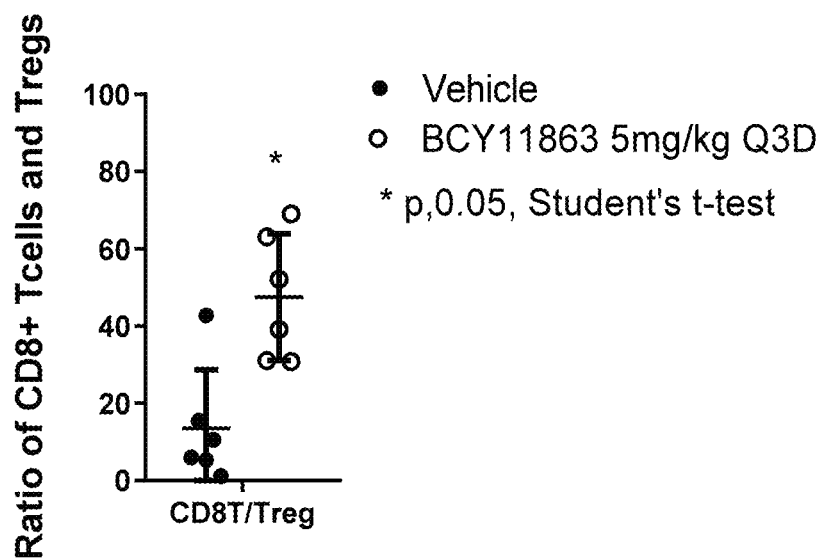
Figure 10:
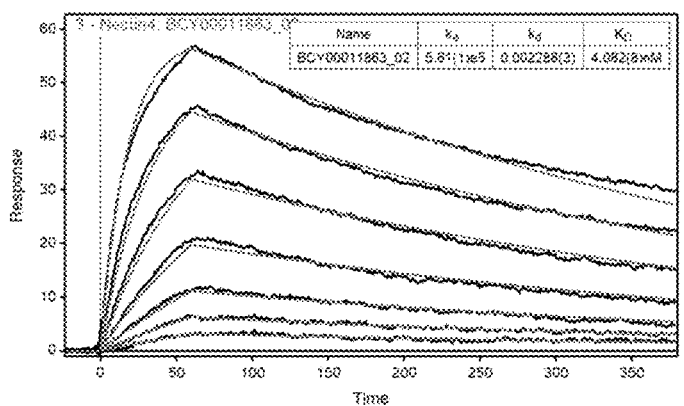
FIG. 10: Surface plasmon resonance (SPR) binding study of BCY11863 to immobilized (A) Nectin-4 and (B) CD137. Dual binding SPR assay immobilizing (C) CD137 and (D) Nectin-4 on the SPR chip followed by capturing BCY11863. The affinity of bound BCY11863 to soluble human Nectin-4 (C) or CD137 (D) is measured by flowing the soluble receptor over the chip at different concentrations. (E) Binding of BCY13582 (biotinylated BCY11863) immobilized on streptavidin SPR chip to soluble human CD137.
Figure 10:
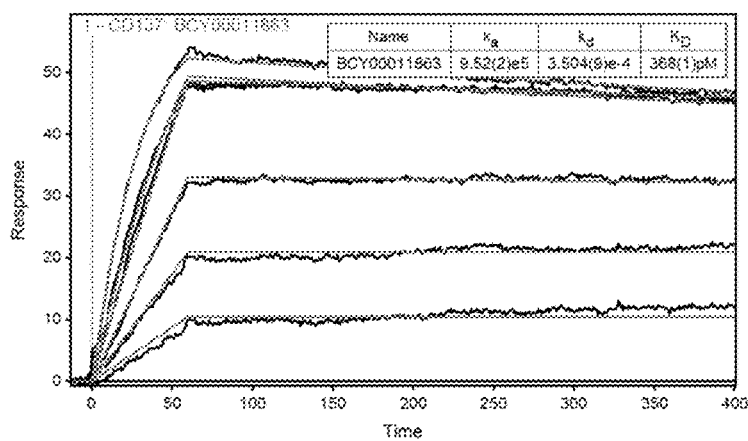
Figure 10:
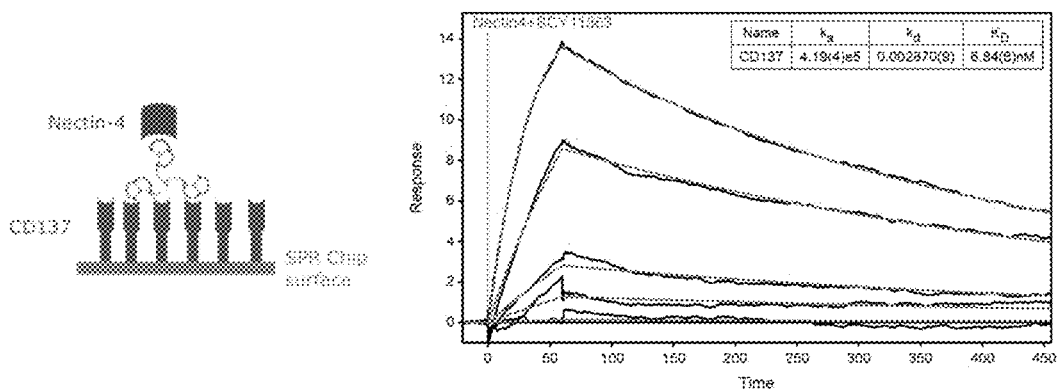
Figure 11:
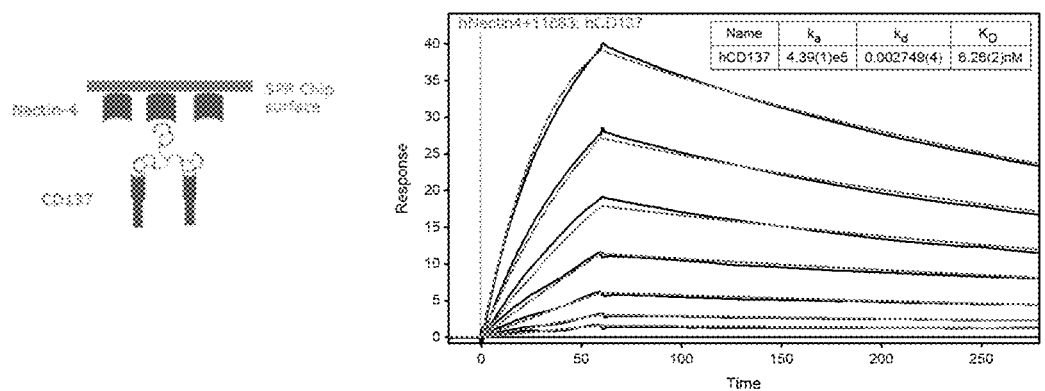
FIG. 11: Retrogenix's cell microarray technology used to explore non-specific off target interactions of BCY13582 (biotinylated BCY11863). Shown here is screening data that shows that 1 μM of BCY13582 added to microarray slides expressing 11 different proteins only binds to CD137 and Nectin-4 (detected using AlexaFluor647 labelled streptavidin). The binding signal is displaced when incubated with BCY11863.
Figure 11:
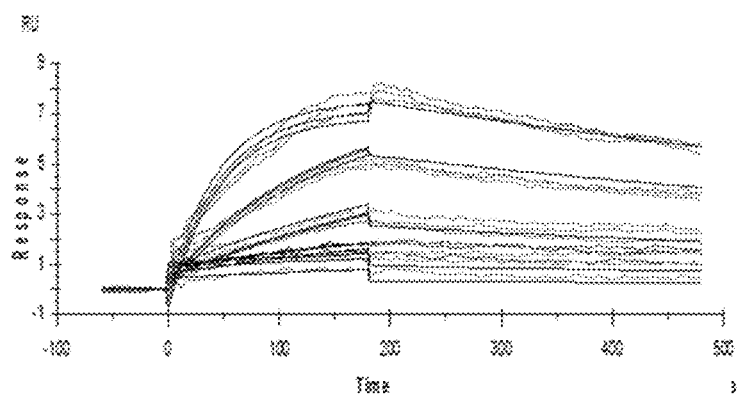
Figure 11:
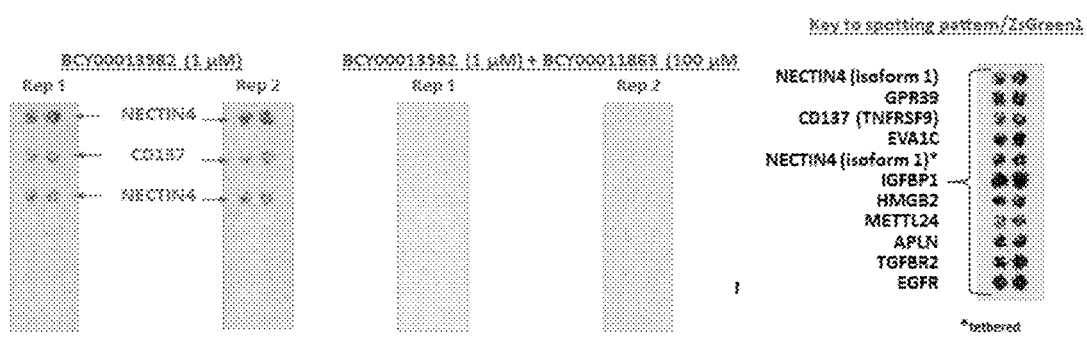
Figure 12:
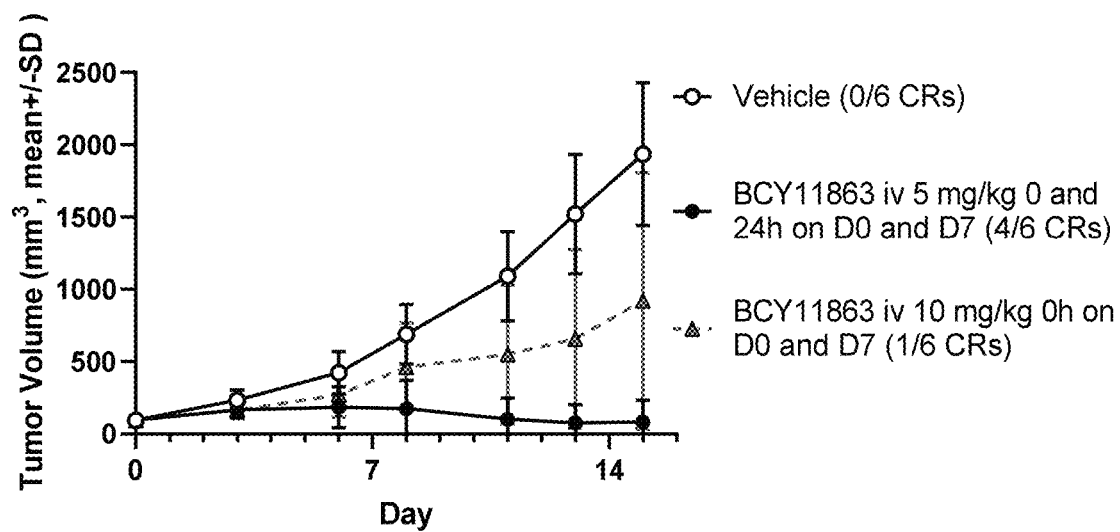
FIG. 12: Tumor growth curves of MC38#13 tumors in huCD137 C57Bl/6 mice demonstrate the anti-tumor activity of BCY11863 after different doses and dose intervals. The number of complete responder animals (CR; no palpable tumor) on day 15 after treatment initiation is indicated in parentheses.
Figure 13:
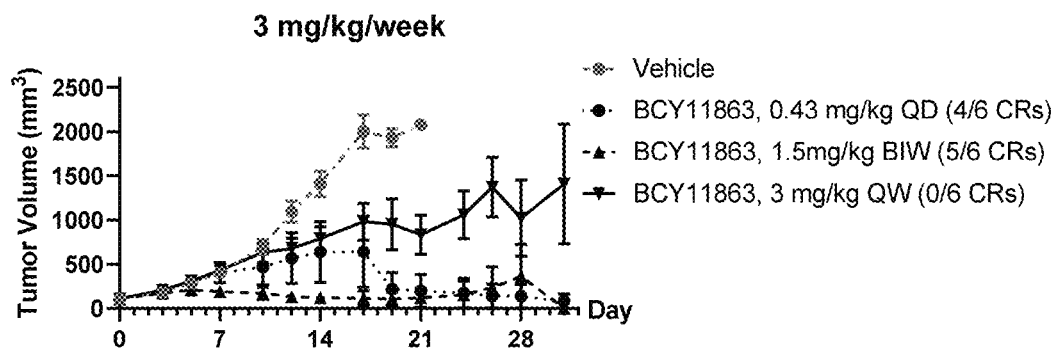
FIG. 13: Tumor growth curves (mean±SEM) of MC38#13 tumors (n=6/cohort) in huCD137 C57Bl/6 mice demonstrate the anti-tumor activity of BCY11863 at different doses and dose schedules. The number of complete responder animals (CR; no palpable tumor) on day 52 after treatment initiation is indicated in parentheses. (A) Cohorts dosed with vehicle or 3 mg/kg total weekly dose of BCY11863. (B) Cohorts dosed with vehicle or 10 mg/kg total weekly dose of BCY11863. (C) Cohorts dosed with vehicle or 30 mg/kg total weekly dose of BCY11863.
Figure 13:
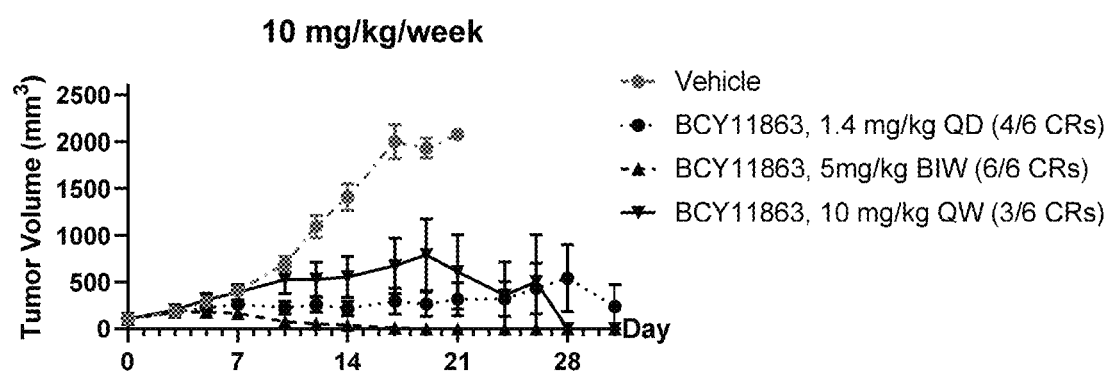
Figure 13:
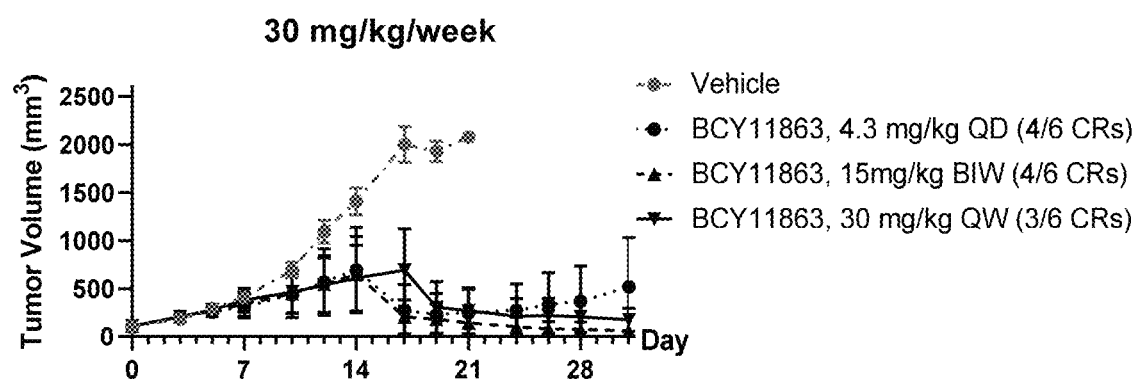

Data is presented herein in FIG. 1 and Table 1 which shows that BCY11863 demonstrated strong CD137 activation in a CD137 reporter assay. In addition, data is presented herein in FIG. 2 and Table 2 which shows that BCY11863 induces robust IL-2 and IFN-γ cytokine secretion in a PBMC co-culture assays with multiple tumor cell lines and human PBMC donors. Furthermore, data is presented herein in FIG. 3 and Table 5 which shows that BCY11863 demonstrated an excellent PK profile with a terminal half-life of 4.1 hours in SD Rats and 5.3 hours in cyno. Data shown in FIGS. 10 and 11 along with methods section 11 and 12 demonstrate binding and exquisite selectivity of BCY11863 for its target Nectin-4 and CD137. FIGS. 4 and 5 demonstrate profound anti-tumor activity of BCY11863 in MC38#13 syngeneic mice and the formation of immunogenic memory after BCY11863 treatment. FIGS. 6 and 7 demonstrate anti-tumor activity of BCY11863 in CT26#7 syngeneic model with corresponding infiltration of cytotoxic T cells into the tumor. FIGS. 12 and 13 clearly demonstrate that BCY11863 does not have to maintain measurable plasma concentrations as dosing with 1.5 mg/kg BIW and 5 mg/kg at 0, 24 h in a week produced robust anti-tumor activity.

Reference herein is made to certain analogues (i.e. modified derivatives) and metabolites of BCY11863, each of which form additional aspects of the invention and are summarised in Table B below:

TABLE B

Composition of BCY11863 analoques and metabolites

| Complex No. | Nectin-4 BCY No. | Attachment Point | Linker | CD137 BCY No. | Attachment Point | Modifier |
|---|---|---|---|---|---|---|
| BCY13390 | BCY8116 | N-terminus | N-(acid-PEG$_3$)-N-bis(PEG$_3$-azide) | BCY8928, BCY13389 | dLys(PYA)4 dLys(PYA)4 | |
| BCY13582 | BCY8116 | N-terminus | N-(acid-PEG$_3$)-N-bis(PEG$_3$-azide) | BCY8928, BCY13389 | dLys(PYA)4 dLys(PYA)4 | Biotin-Peg 12 |
| BCY13583 | BCY8116 | N-terminus | N-(acid-PEG$_3$)-N-bis(PEG$_3$-azide) | BCY8928, BCY13389 | dLys(PYA)4 dLys(PYA)4 | Alexa Fluor 488 |
| BCY13628 | BCY8116 | N-terminus | N-(acid-PEG$_3$)-N-bis(PEG$_3$-azide) | BCY8928, BCY13389 | dLys(PYA)4 dLys(PYA)4 | Cyanine 5 |
| BCY15155 | BCY8116 | N-terminus | N-(acid-PEG$_3$)-N-bis(PEG$_3$-azide) | BCY8928, BCY14601 | dLys(PYA)4 dLys(PYA)4 | |
| BCY14602 | BCY8116 | N-terminus | N-(acid-PEG$_3$)-N-bis(PEG$_3$-azide) | BCY14601 | dLys(PYA)4 | | wherein BCY14601 represents a bicyclic peptide ligand having the sequence of C$_i$[tBuAla]PE[D-Lys(PYA)]PYC$_{ii}$-FADPY[Nle]C$_{iii}$-A (SEQ ID NO: 3) with TATA as a molecular scaffold;

and wherein BCY13389 represents a bicyclic peptide ligand having the sequence of [Ac]C$_i$[tBuAla]PE[D-Lys(PYA)]PYC$_{ii}$FADPY[Nle]C$_{iii}$-K (SEQ ID NO: 4) with TATA as a molecular scaffold.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature
Numbering

When referring to amino acid residue positions within compounds of the invention, cysteine residues (C$_i$, C$_{ii}$ and C$_{iii}$) are omitted from the numbering as they are invariant, therefore, the numbering of amino acid residues within SEQ ID NO: 1 is referred to as below:

(SEQ ID NO: 1)
C$_i$-P$_1$-1Nal$_2$-dD$_3$-C$_{ii}$-M$_4$-HArg$_5$-D$_6$-W$_7$-S$_8$-T$_9$-P$_{10}$-

HyP$_{11}$-W$_{12}$-C$_{iii}$.

For the purpose of this description, the bicyclic peptides are cyclised with 1,1',1"-(1,3,5-triazinane-1,3,5-triyl) triprop-2-en-1-one (TATA) and yielding a tri-substituted structure. Cyclisation with TATA occurs on C$_i$, C$_{ii}$, and C$_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

βAla-Sar10-A-(SEQ ID NO: X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa). For the avoidance of doubt, references to amino acids either as their full name or as their amino acid single or three letter codes are intended to be represented herein as L-amino acids unless otherwise stated. If such an amino acid is intended to be represented as a D-amino acid then the amino acid will be prefaced with a lower case d within square parentheses, for example [dA], [dD], [dE], [dK], [d1Nal], [dNle], etc.

Advantages of the Peptide Ligands

Certain heterotandem bicyclic peptide complexes of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Heterotandem bicyclic peptide complexes should ideally demonstrate stability to plasma proteases, epithelial ("membrane-anchored") proteases, gastric and intestinal proteases, lung surface proteases, intracellular proteases and the like. Protease stability should be maintained between different species such that a heterotandem bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

Selectivity. Certain heterotandem bicyclic peptide complexes of the invention demonstrate good selectivity over other targets;

An optimal plasma half-life in the circulation. Depending upon the clinical indication and treatment regimen, it may be required to develop a heterotandem bicyclic peptide complex for short exposure in an acute illness management setting, or develop a heterotandem bicyclic peptide complex with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Crucially, data is presented herein where the heterotandem bicyclic peptide complex of the invention demonstrates anti-tumor efficacy when dosed at a frequency that does not maintain plasma concentrations above the in vitro EC$_{50}$ of the compound. This is in contrast to larger recombinant biologic (i.e. antibody based) approaches to CD137 agonism or bispecific CD137 agonism (Segal et al., Clin Cancer Res., 23(8):1929-1936 (2017), Claus et al., Sci Trans Med., 11 (496): eaav5989, 1-12 (2019), Hinner et al., Clin Cancer Res., 25(19):5878-5889 (2019)). Without being bound by theory, the reason for this observation is thought to be due to the fact that heterotandem bicycle complexes have relatively low molecular weight (typically <15 kDa), they are fully synthetic and they are tumor targeted agonists of CD137. As such, they have relatively short plasma half lives but good tumor penetrance and retention. Data is presented herein which fully supports these advantages. For example, anti-tumor efficacy in syngeneic rodent models in mice with humanized CD137 is demonstrated either daily or every 3$^{rd}$ day. In addition, intraperitoneal pharmacokinetic data shows that the plasma half life is <3 hours, which would predict that the circulating concentration of the complex would consistently drop below the in vitro EC$_{50}$ between doses. Furthermore, tumor pharmacokinetic data shows that levels of heterotandem bicycle complex in tumor tissue may be higher and more sustained as compared to plasma levels.

It will be appreciated that this observation forms an important further aspect of the invention. Thus, according to a further aspect of the invention, there is provided a method of treating cancer which comprises administration of a heterotandem bicyclic peptide complex as defined herein at a dosage frequency which does not sustain plasma concentrations of said complex above the in vitro $EC_{50}$ of said complex.

Immune Memory. Coupling the cancer cell binding bicyclic peptide ligand with the immune cell binding bicyclic peptide ligand provides the synergistic advantage of immune memory. Data is presented herein which demonstrates that the heterotandem bicyclic peptide complex of the invention not only eradicates tumors but upon readministration of the tumorigenic agent, none of the inoculated complete responder mice developed tumors (see FIG. 5). This indicates that treatment with the selected heterotandem bicyclic peptide complex of the invention has induced immunogenic memory in the complete responder mice. This has a significant clinical advantage in order to prevent recurrence of said tumor once it has been initially controlled and eradicated.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three reactive groups selected from cysteine, 3-mercaptopropionic acid and/or cysteamine and form at least two loops on the scaffold.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{ii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Ca-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons. (for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{121}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptides to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptides, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

According to a further aspect of the invention, there is provided a heterotandem bicyclic peptide complex as defined herein for use in preventing, suppressing or treating cancer.

Examples of cancers (and their benign counterparts) which may be treated (or inhibited) include, but are not limited to tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and paediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

In general, the heterotandem bicyclic peptide complex of the invention may be prepared in accordance with the following general method:

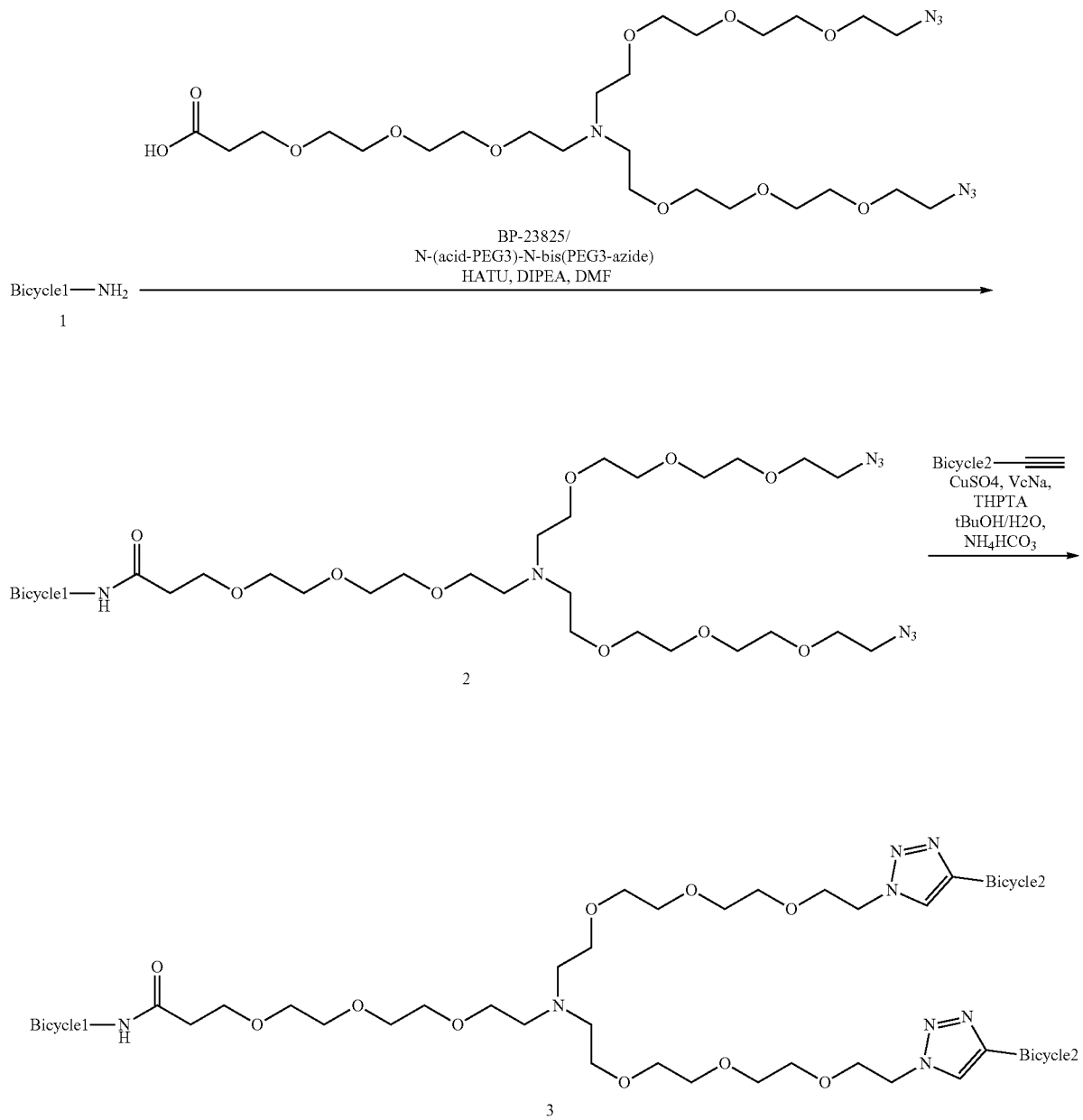

All solvents are degassed and purged with $N_2$ 3 times. A solution of BP-23825 (1.0 eq), HATU (1.2 eq) and DIEA (2.0 eq) in DMF is mixed for 5 minutes, then Bicycle1 (1.2 eq.) is added. The reaction mixture is stirred at 40° C. for 16 hr. The reaction mixture is then concentrated under reduced pressure to remove solvent and purified by prep-HPLC to give intermediate 2.

A mixture of intermediate 2 (1.0 eq) and Bicycle2 (2.0 eq) are dissolved in t-BuOH/$H_2O$ (1:1), and then $CuSO_4$ (1.0 eq), VcNa (4.0 eq), and THPTA (2.0 eq) are added. Finally, 0.2 M $NH_4HCO_3$ is added to adjust pH to 8. The reaction mixture is stirred at 40° C. for 16 hr under $N_2$ atmosphere. The reaction mixture was directly purified by prep-HPLC.

More detailed experimental for the heterotandem bicyclic peptide complex of the invention is provided herein below:

Example 1: Synthesis of BCY11863
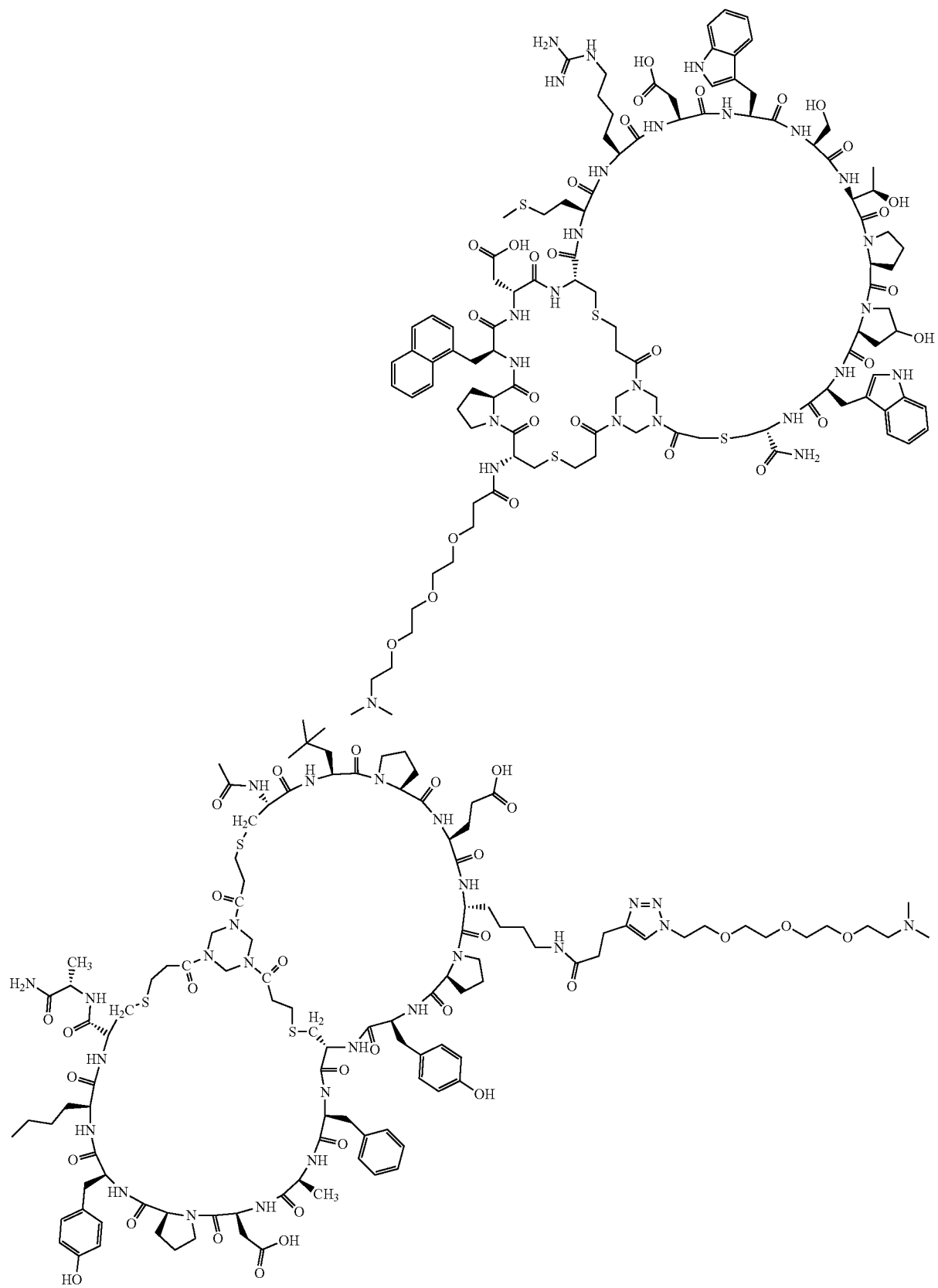
BCY11863

-continued
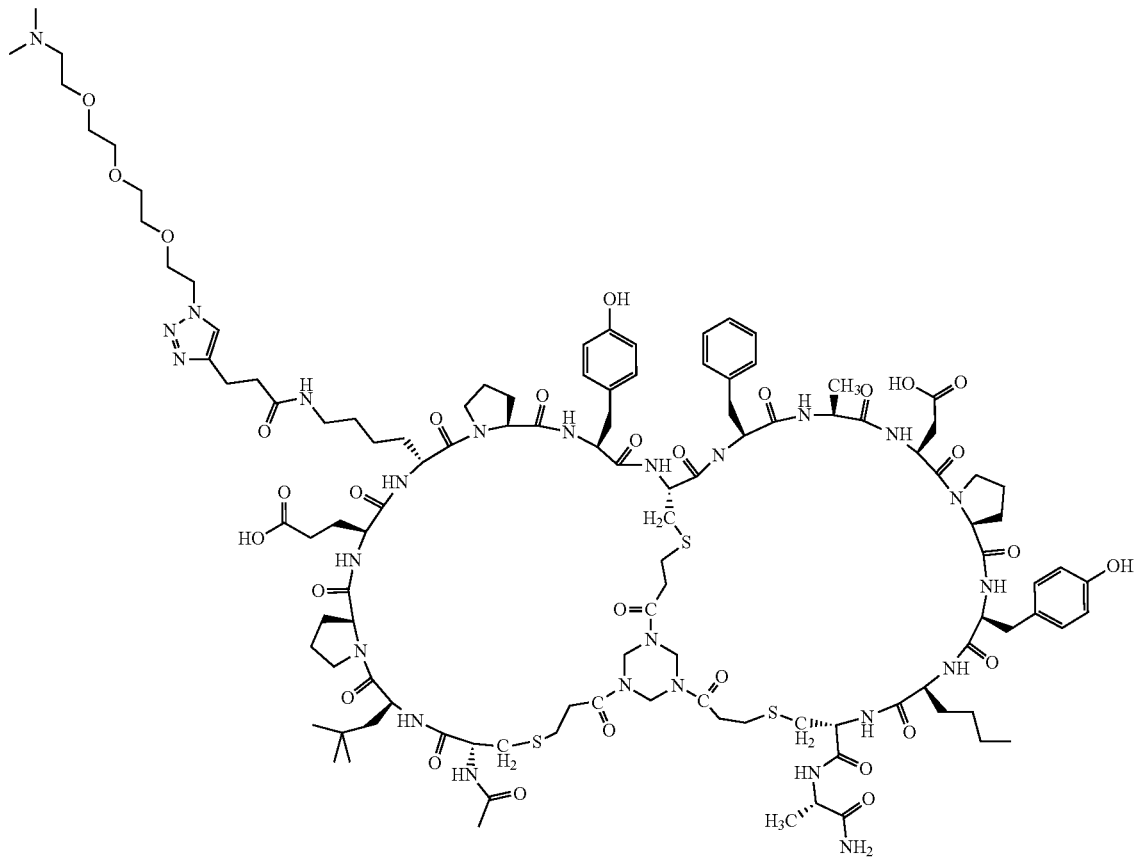 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCCC(=O)N3CN(CN(C3)C(=O)CCSC[C@@H](C(=O)N[C@@H](C)C(N)=O)NC1=O)C(=O)CCSC[C@H](NC(C)=O)C(=O)N[C@@H](CC(C)(C)C)C(=O)N1CCC[C@H]1C(=O)N[C@@H](CCC(=O)O)C(=O)N[C@H](CCCCNC(=O)CCc1cn(CCOCCOCCOCCN(C)C)nn1)C(=O)N1CCC[C@H]1C(=O)N[C@@H](Cc1ccc(O)cc1)C(=O)N2]
Procedure for Preparation of BCY12476
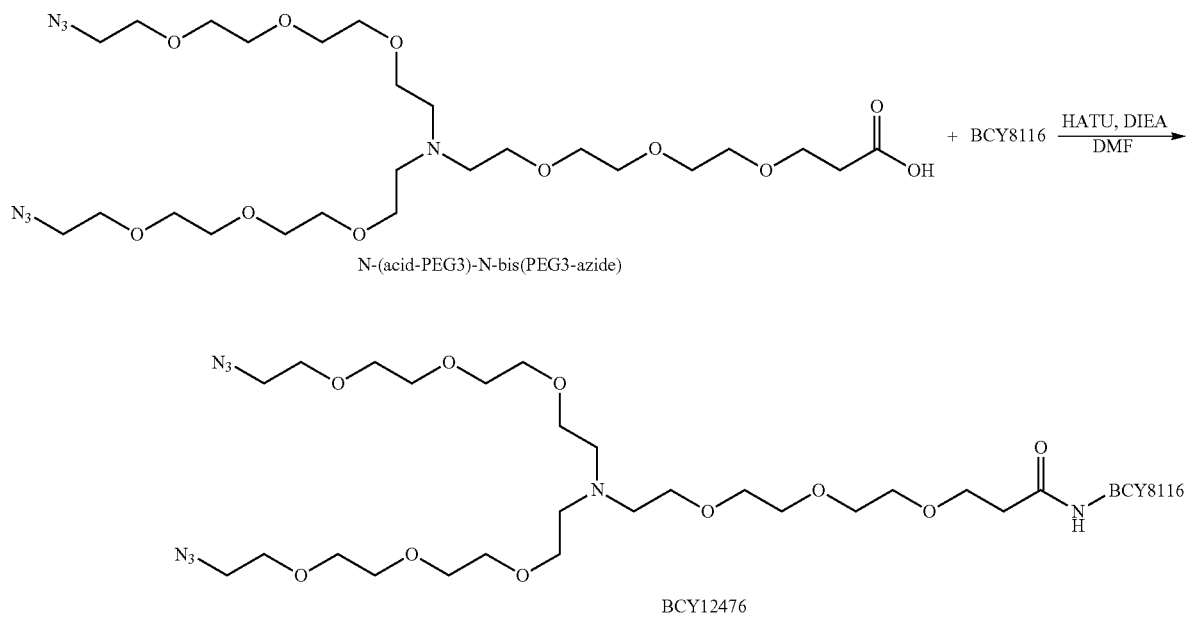

A mixture of N-(acid-PEG3)-N-bis(PEG3-azide) (70.0 mg, 112.2 μmol, 1.0 eq), HATU (51.2 mg, 134.7 μmol, 1.2 eq) and DIEA (29.0 mg, 224.4 μmol, 40 μL, 2.0 eq) was dissolved in DMF (2 mL), and mixed for 5 min. Then BCY8116 (294.0 mg, 135.3 μmol, 1.2 eq) was added. The reaction mixture was stirred at 40° C. for 16 hr. LC-MS showed one main peak with desired m/z. The reaction mixture was concentrated under reduced pressure to remove solvent and produced a residue. The residue was then purified by preparative HPLC. BCY12476 (194.5 mg, 66.02 μmol, 29% yield, 94% purity) was obtained as a white solid. Calculated MW: 2778.17, observed m/z: 1389.3 ([M+2H]$^{2+}$), 926.7 ([M+3H]$^{3+}$).

Procedure for Preparation of BCY11863

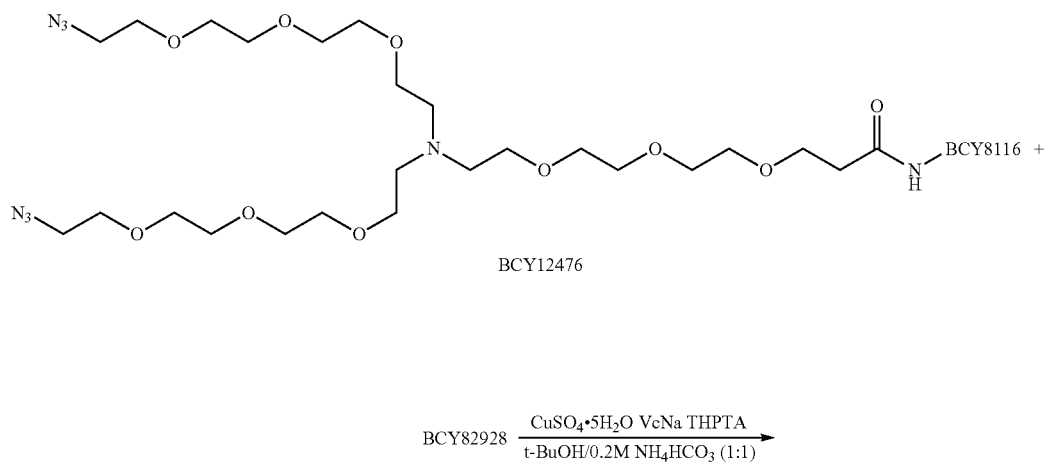

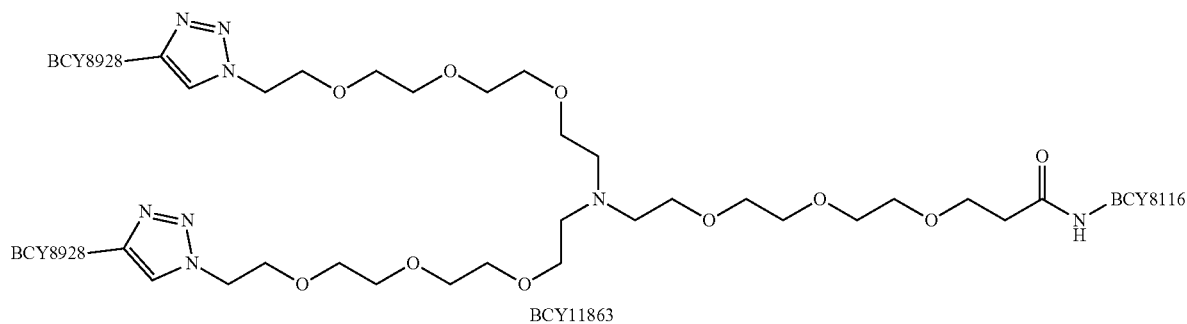

A mixture of BCY12476 (100.0 mg, 36.0 μmol, 1.0 eq), BCY8928 (160.0 mg, 72.0 μmol, 2.0 eq) were first dissolved in 2 mL of t-BuOH/H$_2$O (1:1), and then CuSO$_4$ (0.4 M, 180 μL, 1.0 eq) and VcNa (28.5 mg, 143.8 μmol, 4.0 eq), THPTA (31.2 mg, 71.8 μmol, 2.0 eq) were added. Finally, 0.2 M NH$_4$HCO$_3$ was added to adjust pH to 8. All solvents here were degassed and purged with N$_2$. The reaction mixture was stirred at 40° C. for 16 hr under N$_2$ atmosphere. LC-MS showed BCY8928 remained and desired m/z was also detected. The reaction mixture was directly purified by preparative HPLC. First purification resulted in BCY11863 (117.7 mg, 15.22 μmol, 42.29% yield, 93.29% purity) as TFA salt, while less pure fractions were purified again by preparative HPLC, producing BCY11863 (33.2 mg, 4.3 μmol, 12% yield, 95% purity) as TFA salt. Calculated MW: 7213.32, observed m/z: 1444.0 ([M+5H]$^{5+}$).

Example 2: Synthesis of BCY13390
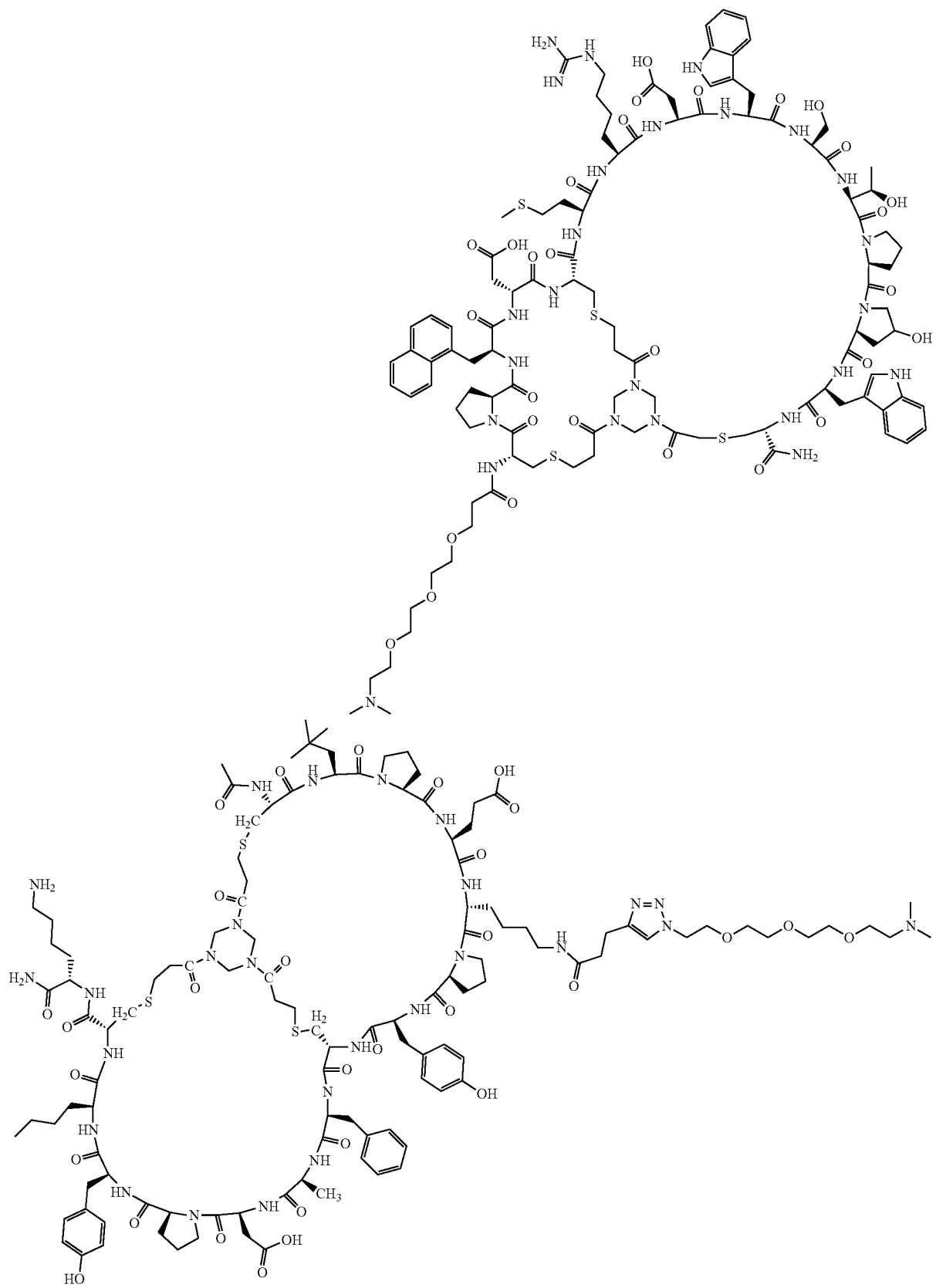
BCY13390

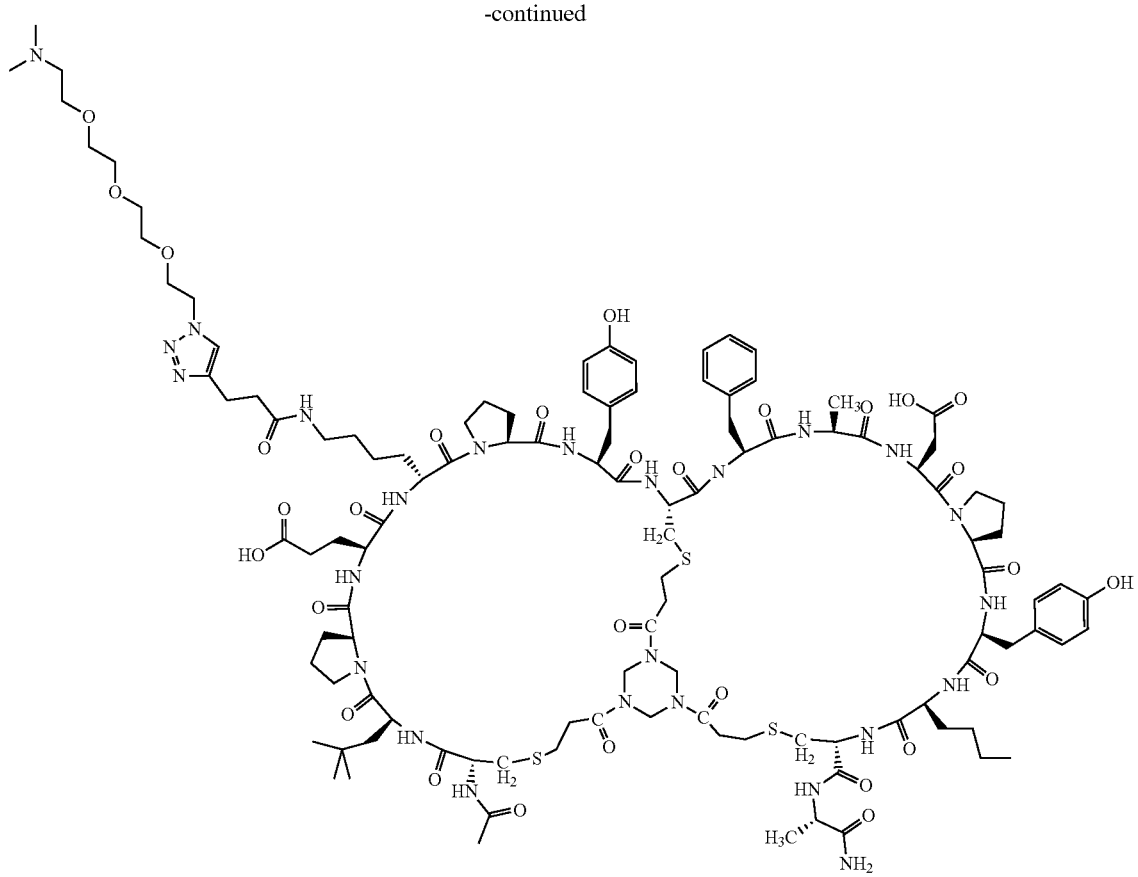
35
Procedure for Preparation of BCY13689
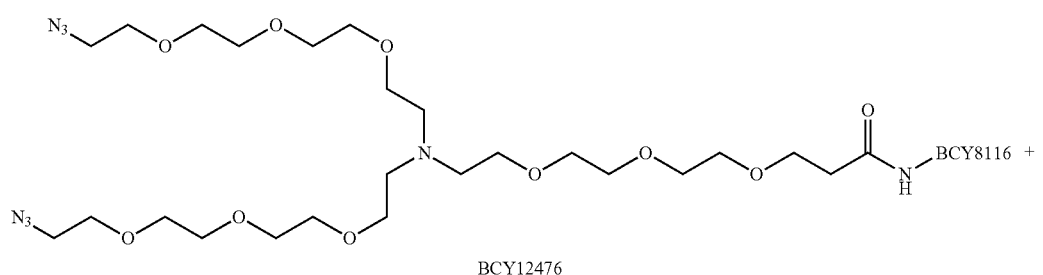
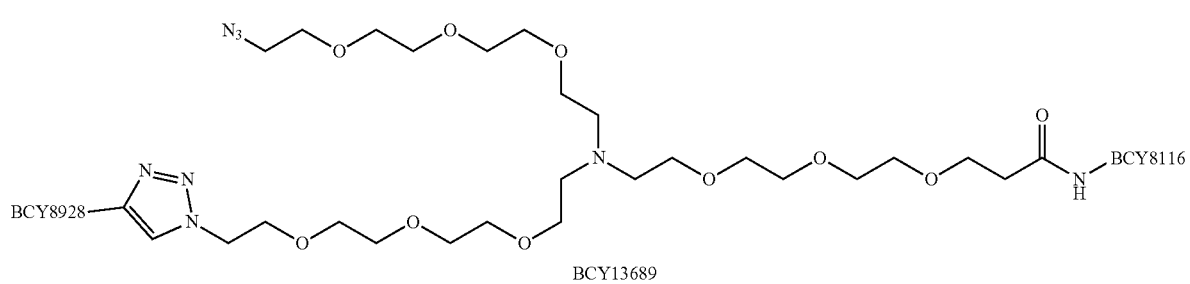

A mixture of BCY12476 (47.0 mg, 16.91 μmol, 1.0 eq), BCY8928 (30.0 mg, 13.53 μmol, 0.8 eq), and THPTA (36.7 mg, 84.55 μmol, 5.0 eq) was dissolved in t-BuOH/H$_2$O (1:1, 8 mL, pre-degassed and purged with N$_2$), and then CuSO$_4$ (0.4 M, 21.0 μL, 0.5 eq) and VcNa (67.0 mg, 338.21 μmol, 20.0 eq) were added under N$_2$. The pH of this solution was adjusted to 8 by dropwise addition of 0.2 M NH$_4$HCO$_3$ (in 1:1 t-BuOH/H$_2$O), and the solution turned light yellow. The reaction mixture was stirred at 25° C. for 1.5 h under N$_2$ atmosphere. LC-MS showed that some BCY12476 remained, BCY8928 was consumed completely, and a peak with the desired m/z was detected. The reaction mixture was filtered and concentrated under reduced pressure to give a residue. The crude product was purified by preparative HPLC, and BCY13689 (25.3 mg, 4.56 μmol, 27% yield, 90% purity) was obtained as a white solid. Calculated MW: 4995.74, observed m/z: 1249.4 ([M+4H]$^{4+}$), 999.9 ([M+5H]$^{5+}$).

Procedure for Preparation of BCY13390

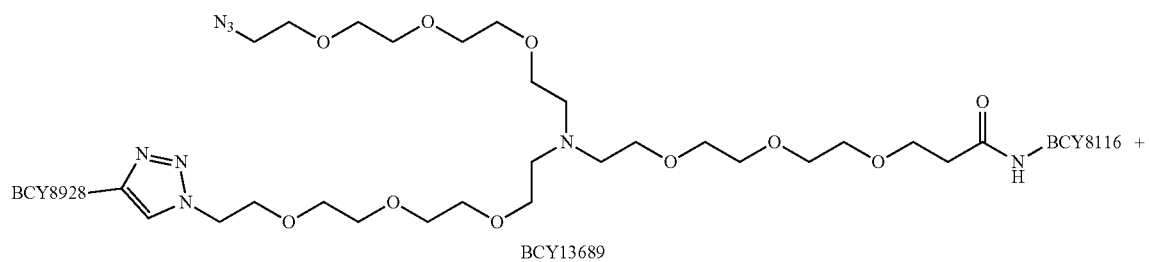

BCY13689

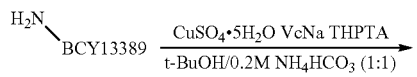

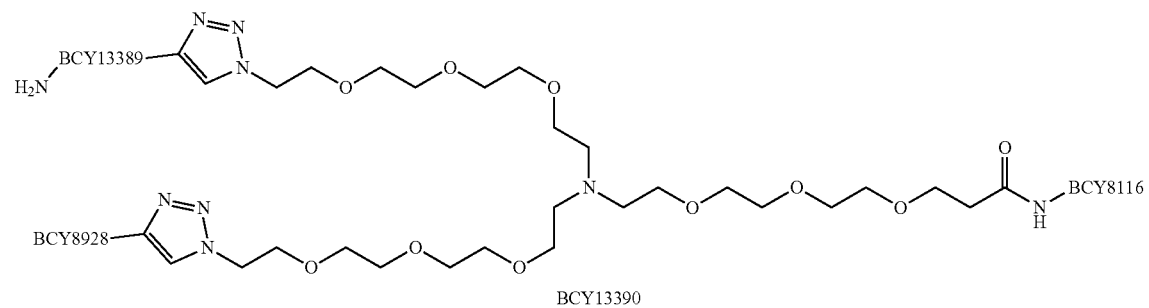

BCY13390

A mixture of BCY13689 (43.6 mg, 8.73 μmol, 1.0 eq), BCY13389 (20.8 mg, 9.16 μmol, 1.05 eq), and THPTA (3.8 mg, 8.73 μmol, 1.0 eq) was dissolved in t-BuOH/H$_2$O (1:1, 1 mL, pre-degassed and purged with N$_2$), and then CuSO$_4$ (0.4 M, 22.0 μL, 1.0 eq) and VcNa (3.5 mg, 17.45 μmol, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25° C. for 2 hr under N$_2$ atmosphere. LC-MS showed a significant peak corresponding to the desired m/z. The reaction mixture was filtered and concentrated under reduced pressure to give a residue. The crude product was purified by preparative HPLC, and BCY13390 (33.8 mg, 4.21 μmol, 48% yield, 90% purity) was obtained as a white solid. Calculated MW: 7270.41, observed m/z: 1454.9 ([M+5H]$^{5+}$), 1213.2 ([M+6H]$^{6+}$).

Example 3: Synthesis of BCY13582
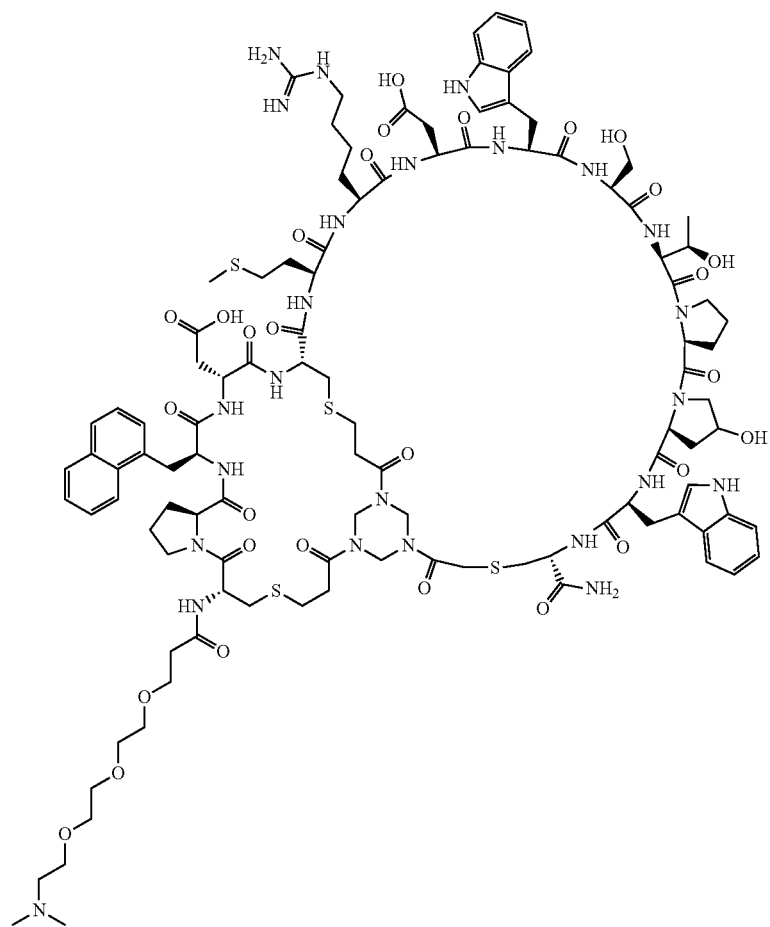
BCY13582

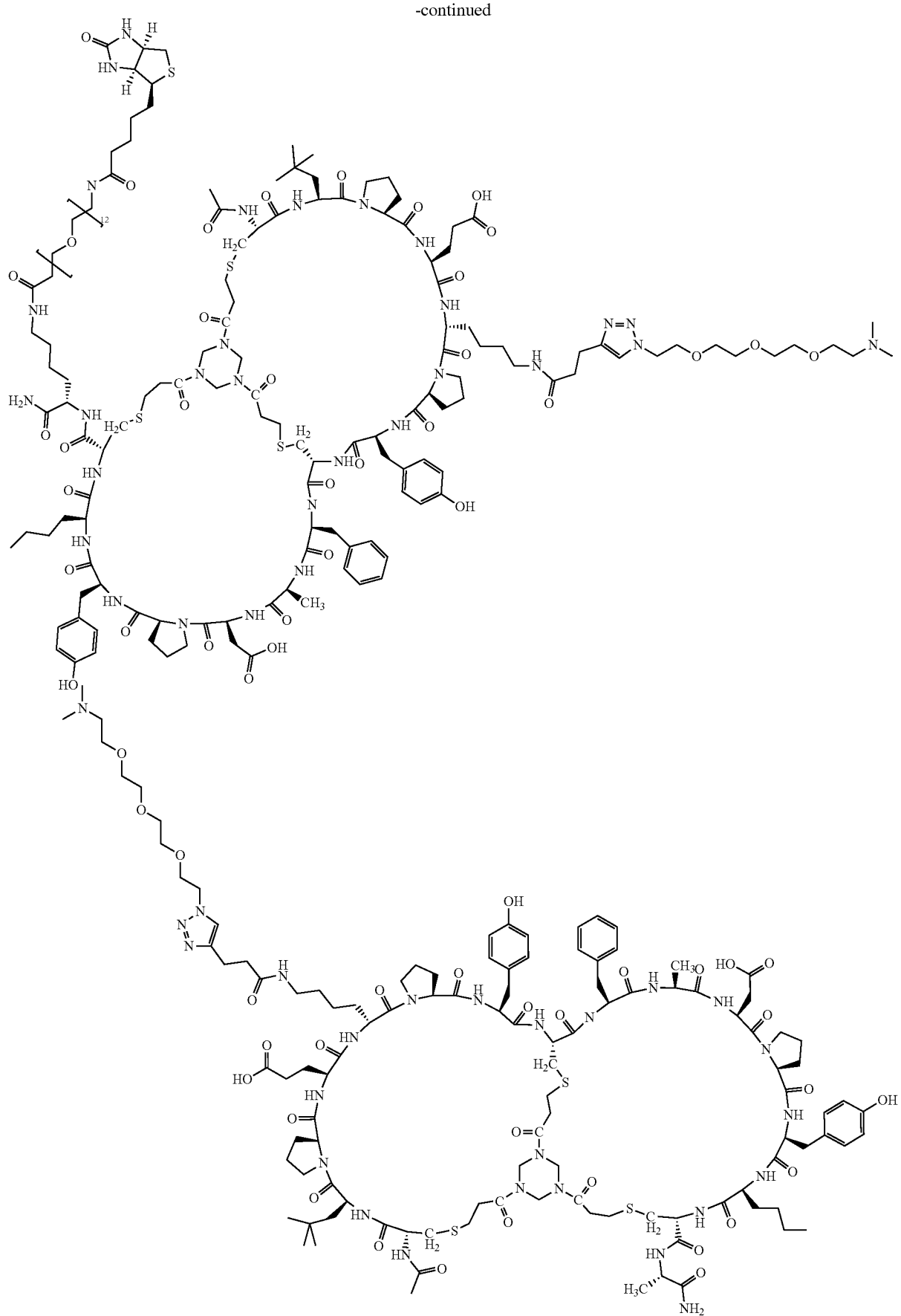

Procedure for Preparation of BCY13582

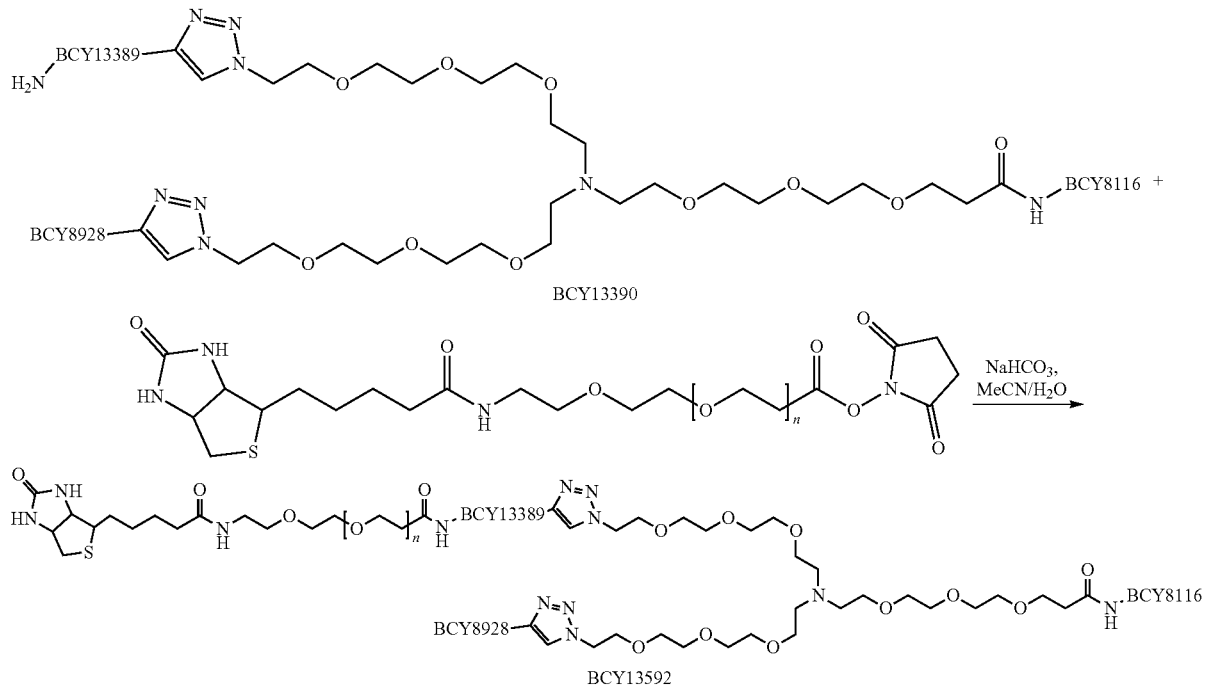

A mixture of BCY13390 (5.0 mg, 0.6 μmol, 1.0 eq), biotin-PEG12-NHS ester (CAS 365441-71-0, 0.7 mg, 0.72 μmol, 1.1 eq) was dissolved in MeCN/H$_2$O (1:1, 2 mL). The pH of this solution was adjusted to 8 by dropwise addition of 1.0 MNaHCO$_3$. The reaction mixture was stirred at 25° C. for 0.5 hr. LC-MS showed BCY13390 was consumed completely, and one main peak with desired m/z was detected. The reaction mixture was filtered and concentrated under reduced pressure to give a residue. The crude product was purified by preparative HPLC, and BCY13582 (2.5 mg, 0.30 μmol, 43% yield, 96% purity) was obtained as a white solid. Calculated MW: 8096.43, observed m/z: 1351.1 ([M+6H]$^{6+}$), 1158.5 ([M+7H]$^{7+}$).

Example 4: Synthesis of BCY13583

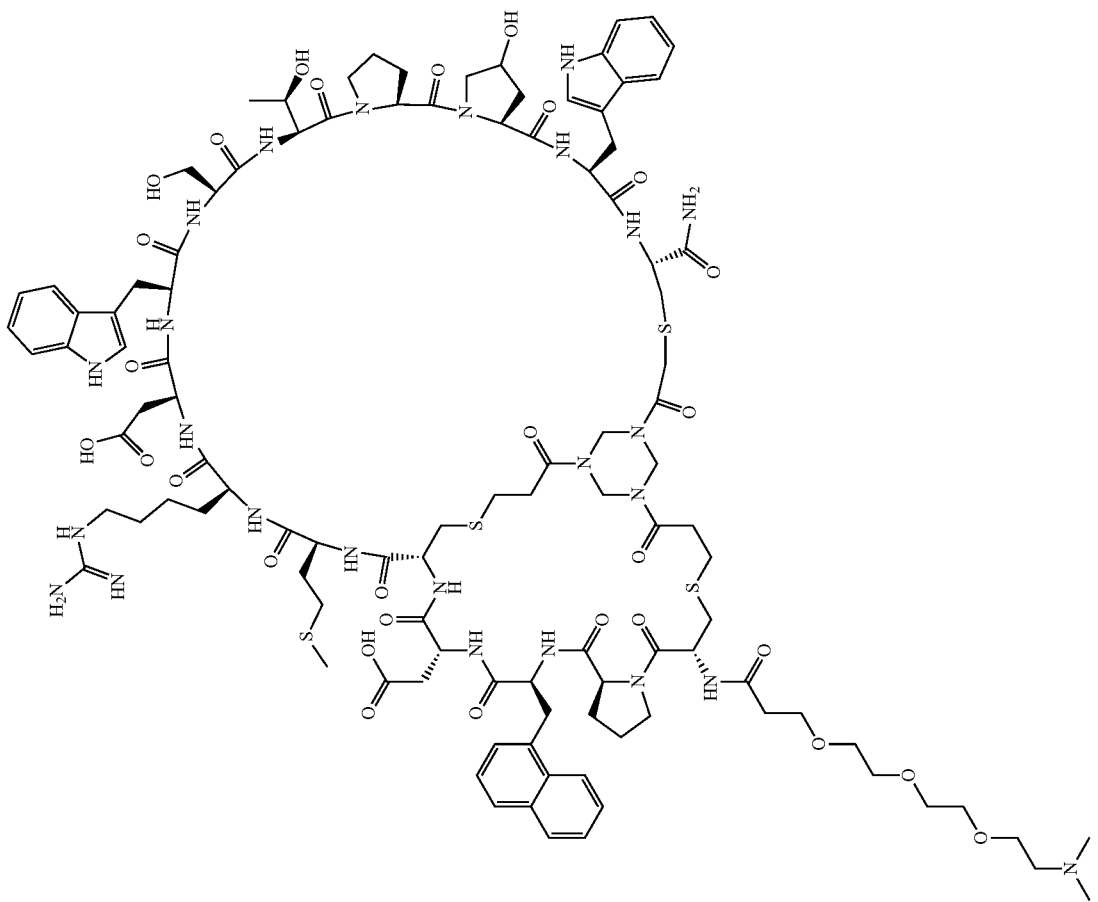

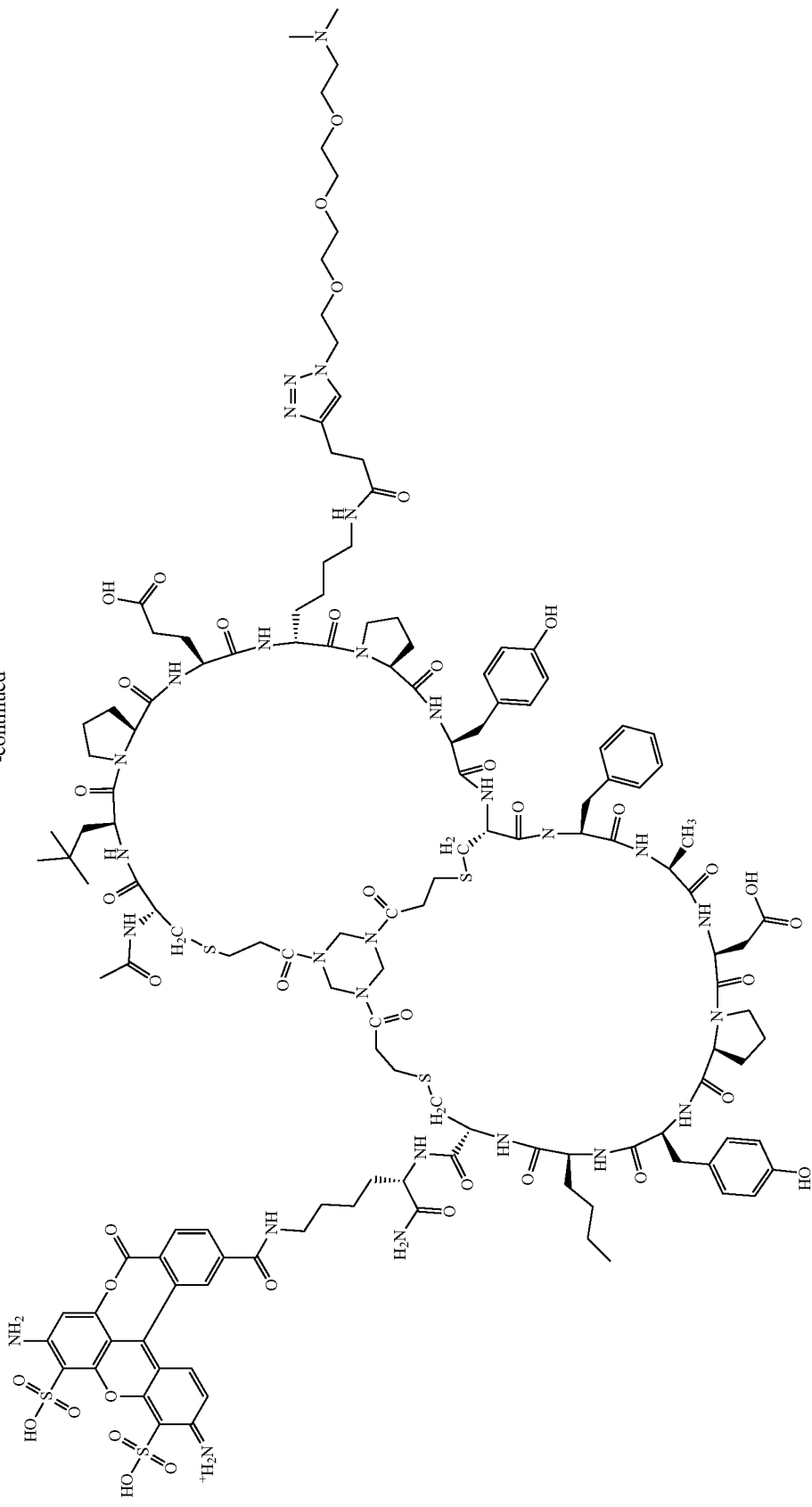

-continued
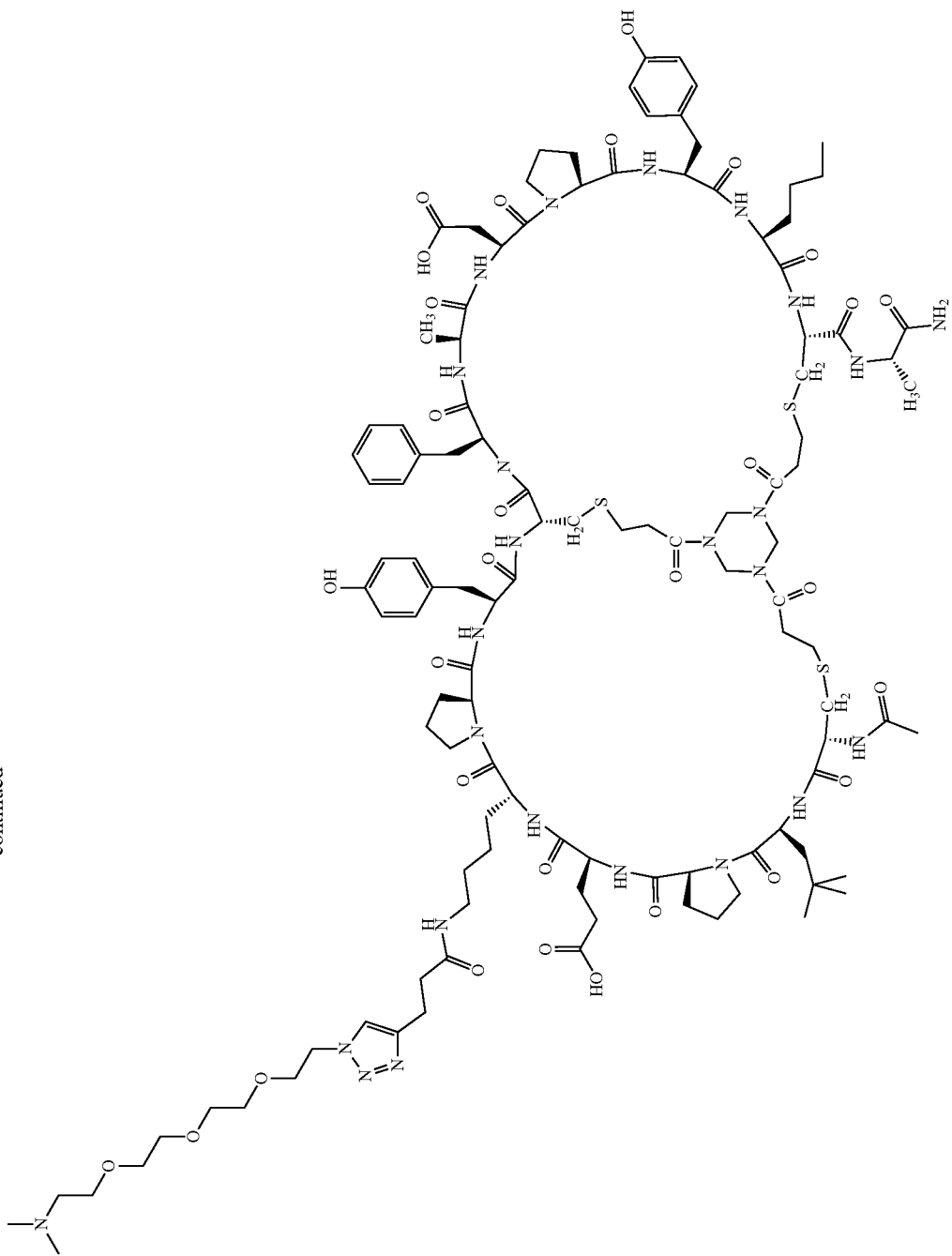

Procedure for Preparation of BCY13583

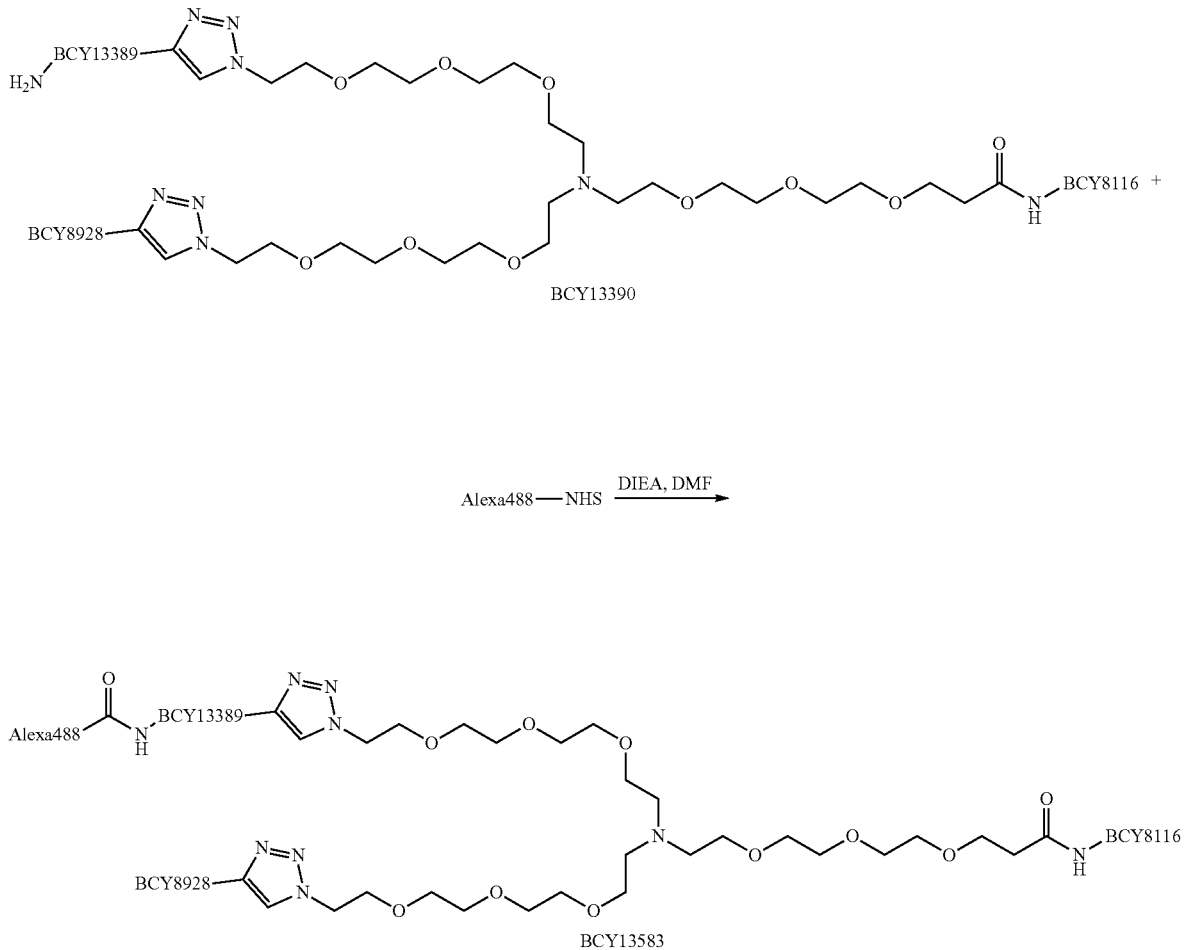

A mixture of BCY13390 (15.0 mg, 2.06 μmol, 1.0 eq) and Alexa Fluor® 488 NHS ester (2.5 mg, 4.12 μmol, 2.0 eq) was dissolved in DMF (0.5 mL). DIEA (2.6 mg, 20.63 μmol, 3.6 μL, 10 eq) was then added dropwise. The reaction mixture was stirred at 25° C. for 1 hr. LC-MS showed BCY13390 remained, and one main peak with desired m/z was detected. Additional Alexa Fluor® 488 NHS ester (2.0 mg, 3.09 μmol, 1.5 eq) was added to the reaction mixture, and the reaction mixture was stirred at 25° C. for one additional hour. HPLC showed BCY13390 was consumed completely. The reaction mixture was filtered and concentrated under reduced pressure to give a residue. The crude product was purified by preparative HPLC, and BCY13583 (5 mg, 0.61 μmol, 29% yield, 95% purity) was obtained as a red solid. Calculated MW: 7787.9, observed m/z: 1948.8 ($[M+4H+H_2O]^{4+}$), 1558.6 ($[M+5H+H_2O]^{5+}$), 1299.1 ($[M+7H+H_2O]^{7+}$).

Example 5: Synthesis of BCY13628
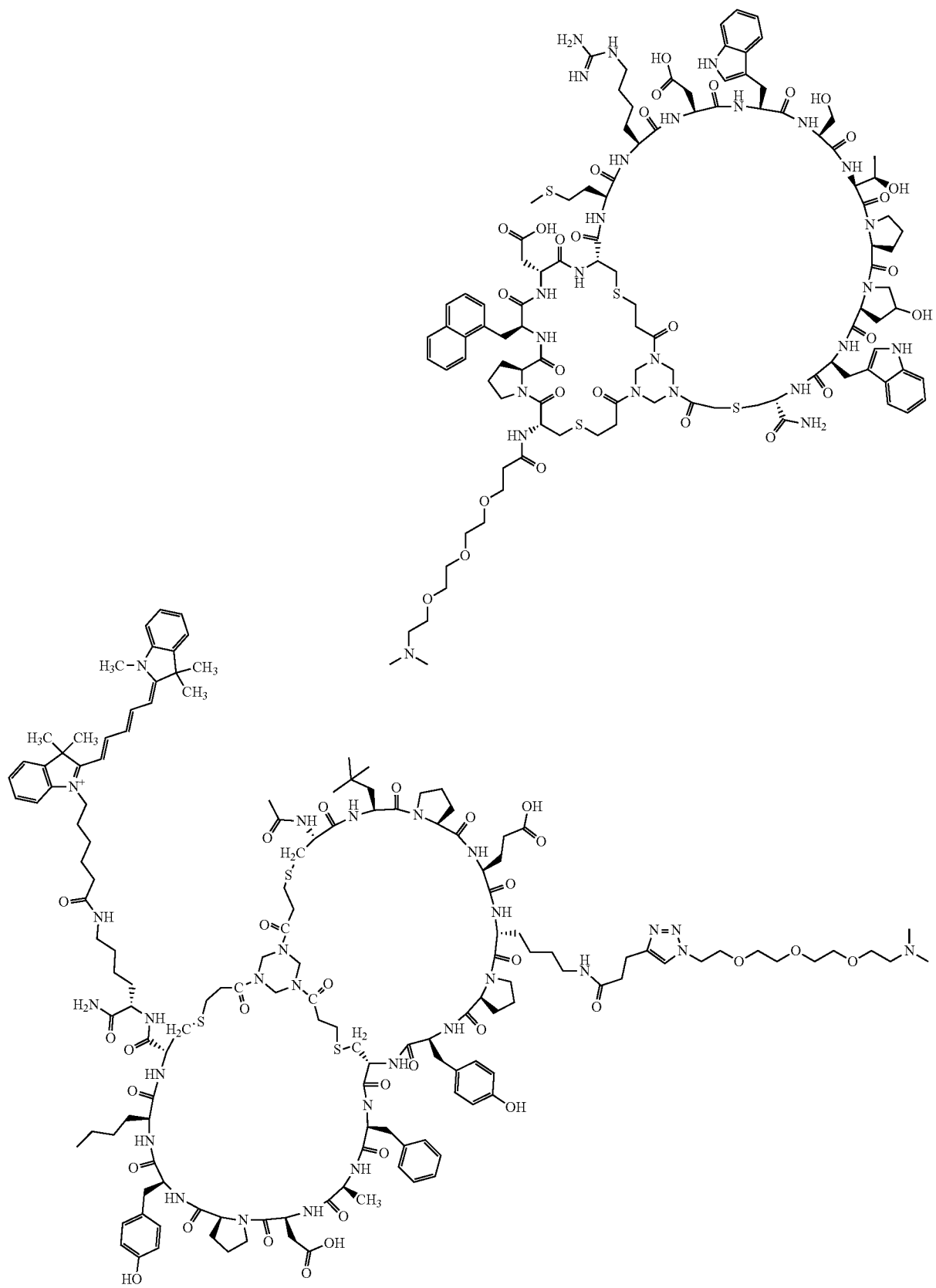

-continued
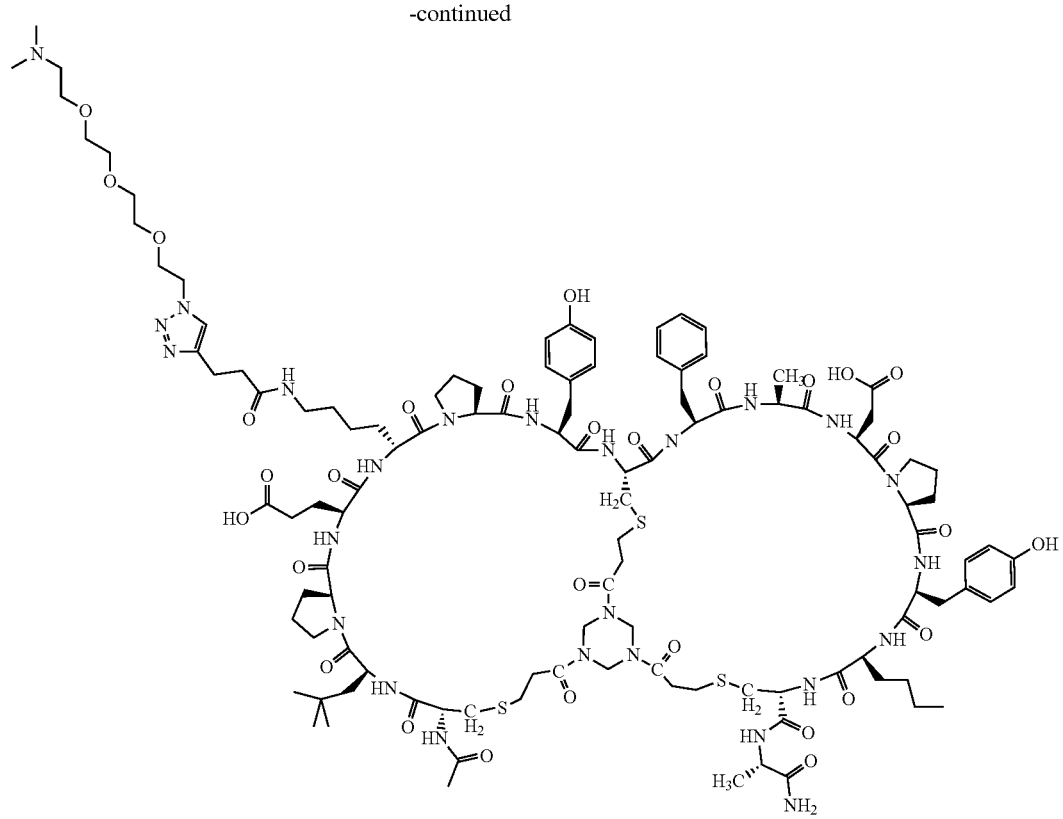
Procedure for Preparation of BCY13628
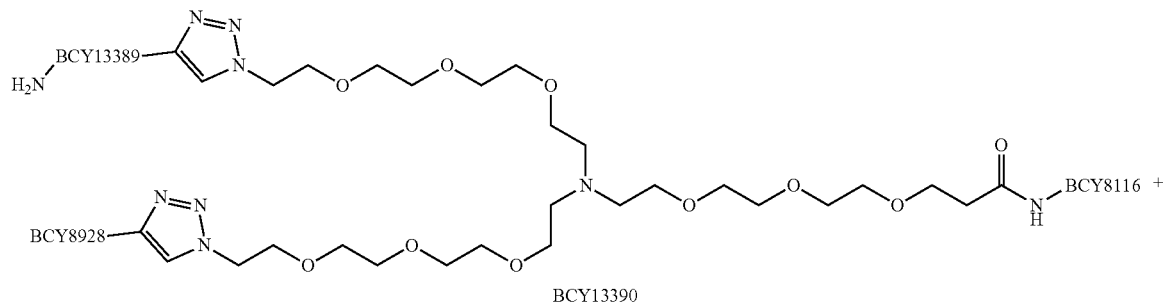
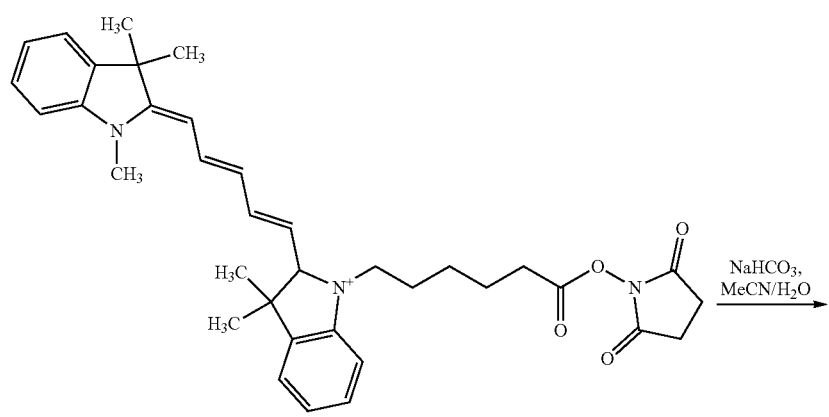

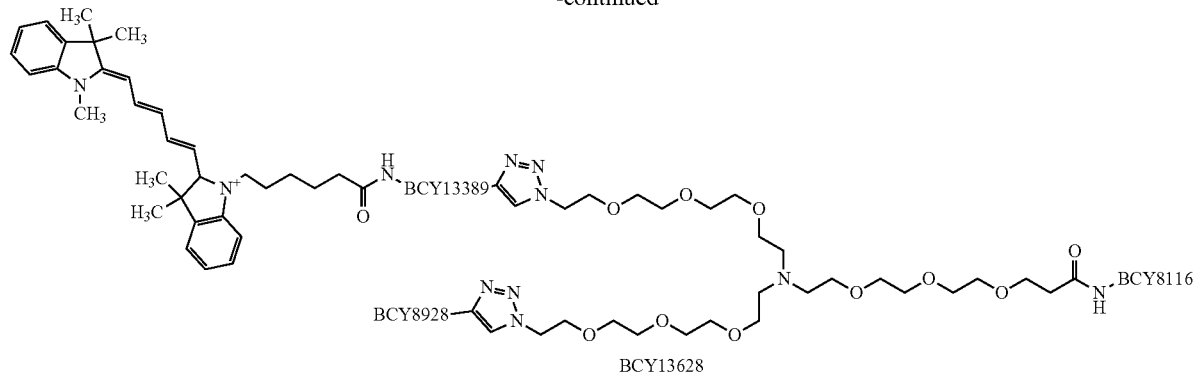

A mixture of BCY13390 (5.6 mg, 0.77 μmol, 1.0 eq) and cyanine 5 NHS ester (0.5 mg, 0.85 μmol, 1.1 eq) was dissolved in MeCN/H$_2$O (1:1, 2 mL). The pH of this solution was adjusted to 8 by dropwise addition of 1.0 M NaHCO$_3$. The reaction mixture was stirred at 25° C. for 0.5 hr. LC-MS showed BCY13390 was consumed completely and one main peak with desired m/z was detected. The reaction mixture was filtered and concentrated under reduced pressure to give a residue. The crude product was purified by preparative HPLC, and BCY13628 (2.9 mg, 0.36 μmol, 46% yield, 95% purity) was obtained as a blue solid. Calculated MW: 7736.06, observed m/z: 1289.9 ([M+6H]$^{6+}$), 1105.5 ([M+7H]$^{7+}$).

Example 6: Synthesis of BCY15155

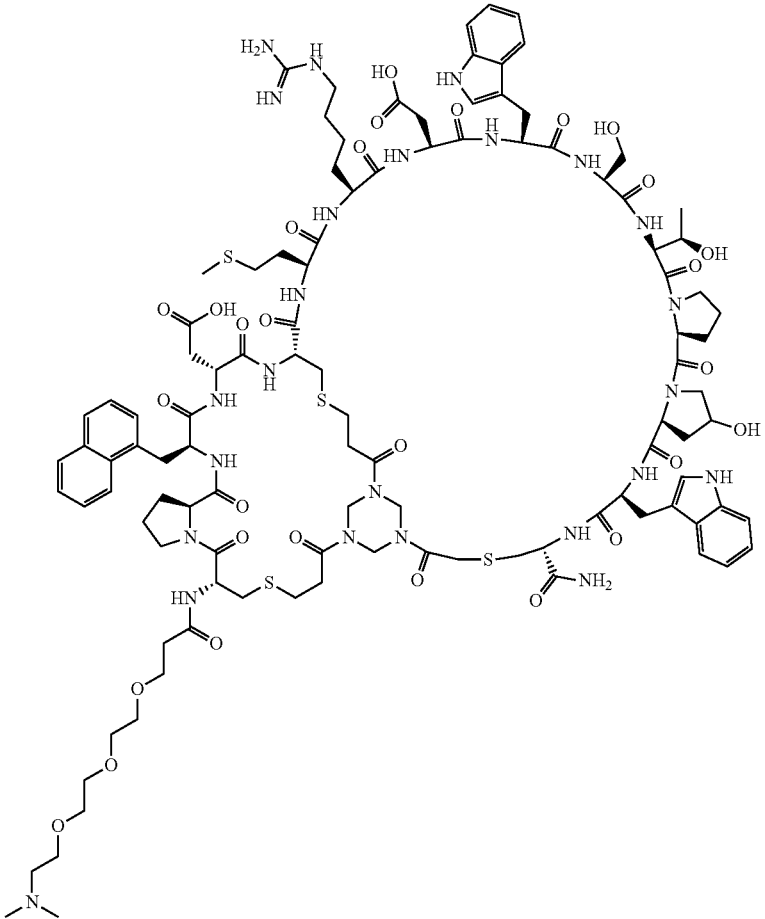

-continued
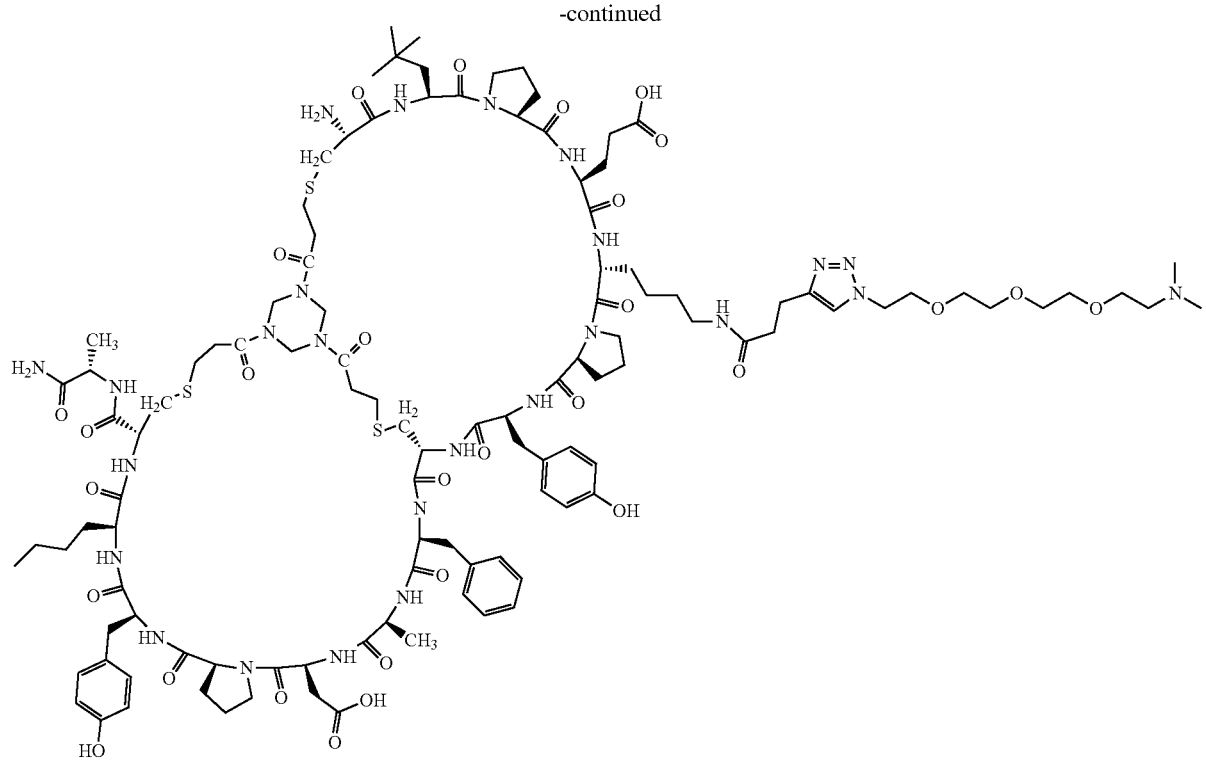
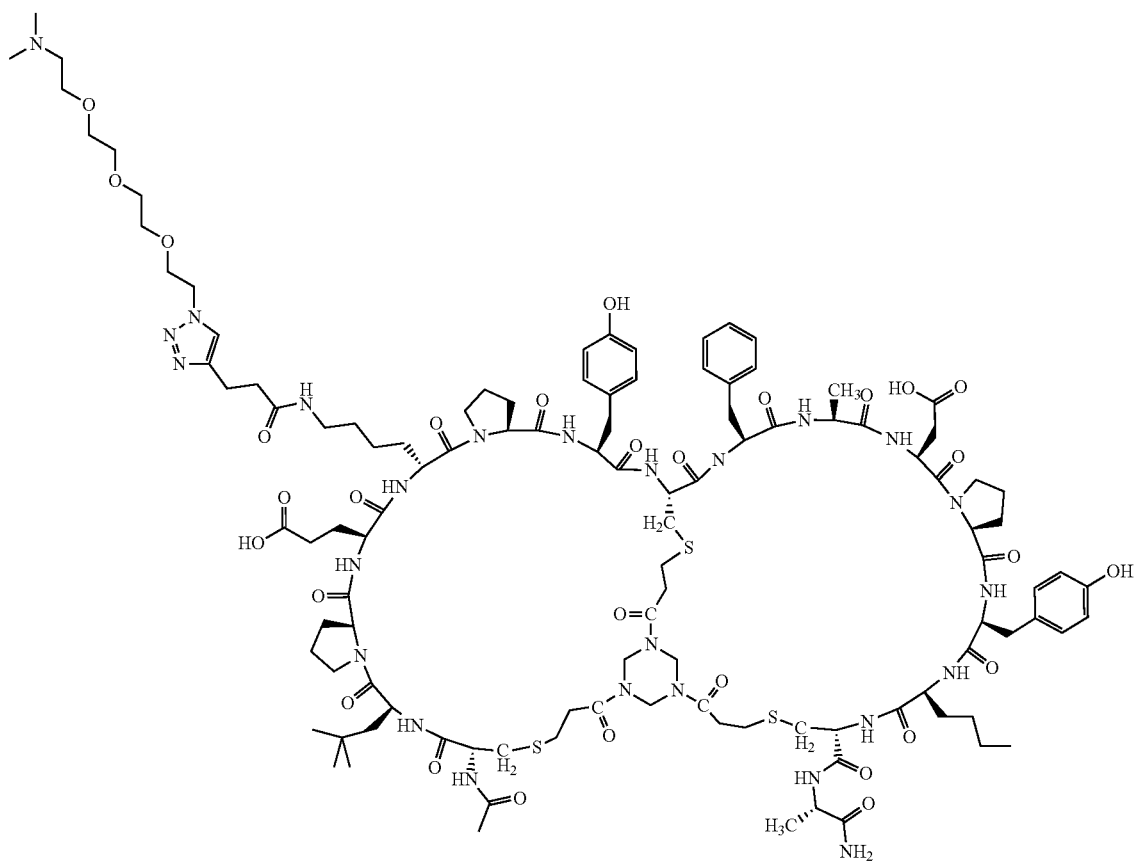 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCCC(=O)N3CN(CN(C3)C(=O)CCSC[C@@H](C(=O)N[C@@H](C)C(N)=O)NC1=O)C(=O)CCSC[C@H](NC(C)=O)C(=O)N[C@@H](CC(C)(C)C)C(=O)N1CCC[C@H]1C(=O)N[C@@H](CCC(=O)O)C(=O)N[C@H](CCCCNC(=O)CCc1cn(CCOCCOCCOCCN(C)C)nn1)C(=O)N1CCC[C@H]1C(=O)N[C@@H](Cc1ccc(O)cc1)C(=O)N2]

Procedure for Preparation of BCY15155

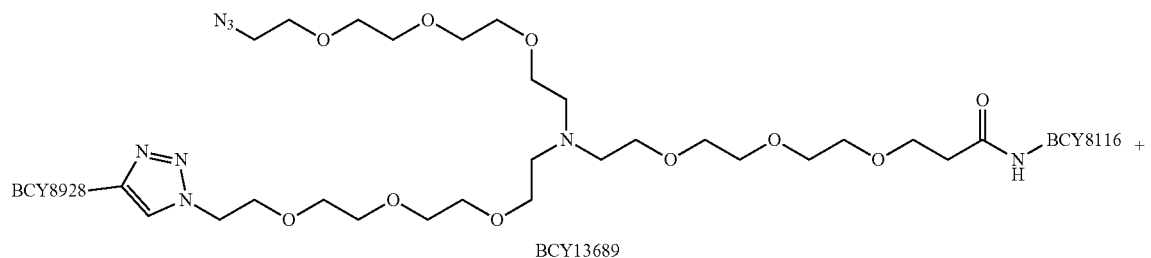

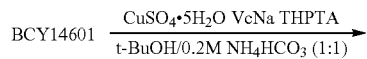

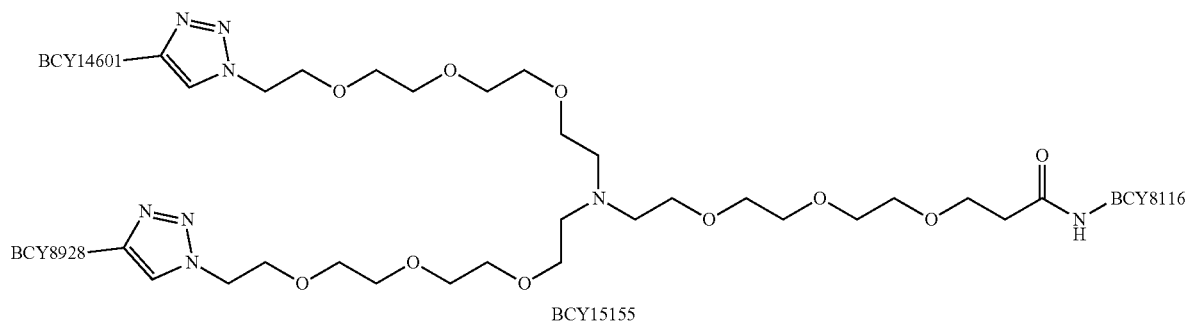

A mixture of BCY13689 (25.0 mg, 5.00 μmol, 1.0 eq), BCY14601 (13.0 mg, 6.01 μmol, 1.2 eq), and THPTA (2.0 mg, 5.00 μmol, 1.0 eq) was dissolved in t-BuOH/0.2 M NH$_4$HCO$_3$ (1:1, 0.5 mL, pre-degassed and purged with N$_2$), and then CUSO$_4$ (0.4 M, 12.5 μL, 1.0 eq) and Vc (3.5 mg, 20.02 μmol, 4.0 eq) were added under N$_2$. The pH of this solution was adjusted to 8, and the solution turned light yellow. The reaction mixture was stirred at 25° C. for 2 hr under N$_2$ atmosphere. LC-MS showed BCY13689 was consumed completely, some BCY14601 remained and one main peak with desired m/z was detected. The reaction mixture was filtered and concentrated under reduced pressure to give a residue. The crude product was purified by preparative HPLC, and BCY15155 (19.7 mg, 2.41 μmol, 36% yield, 97% purity) was obtained as a white solid. Calculated MW: 7171.3, observed m/z: 1434.7 ([M+5H]$^{5+}$), 1196.2 ([M+6H]$^{6+}$).

Example 7: Synthesis of BCY14602
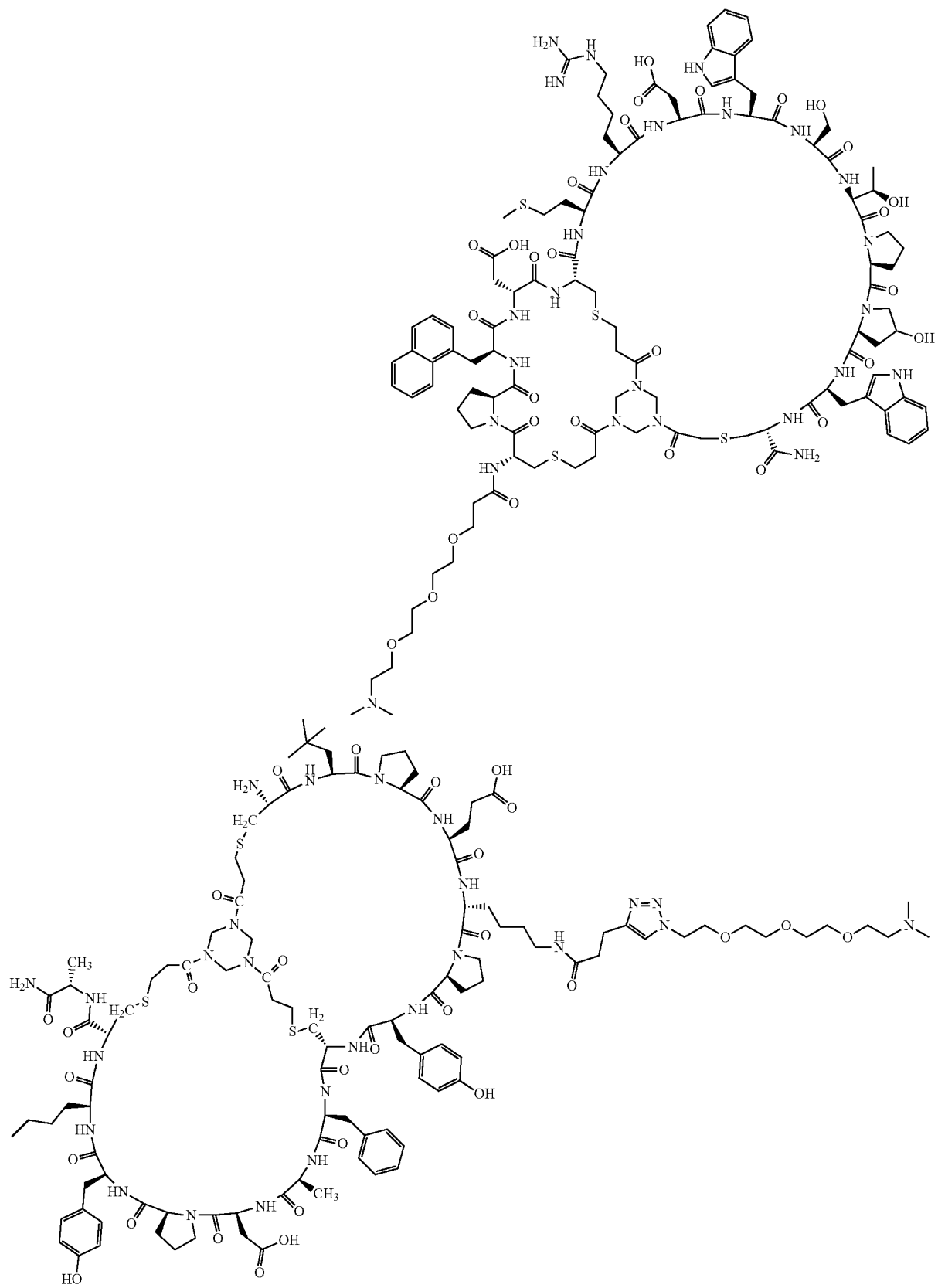

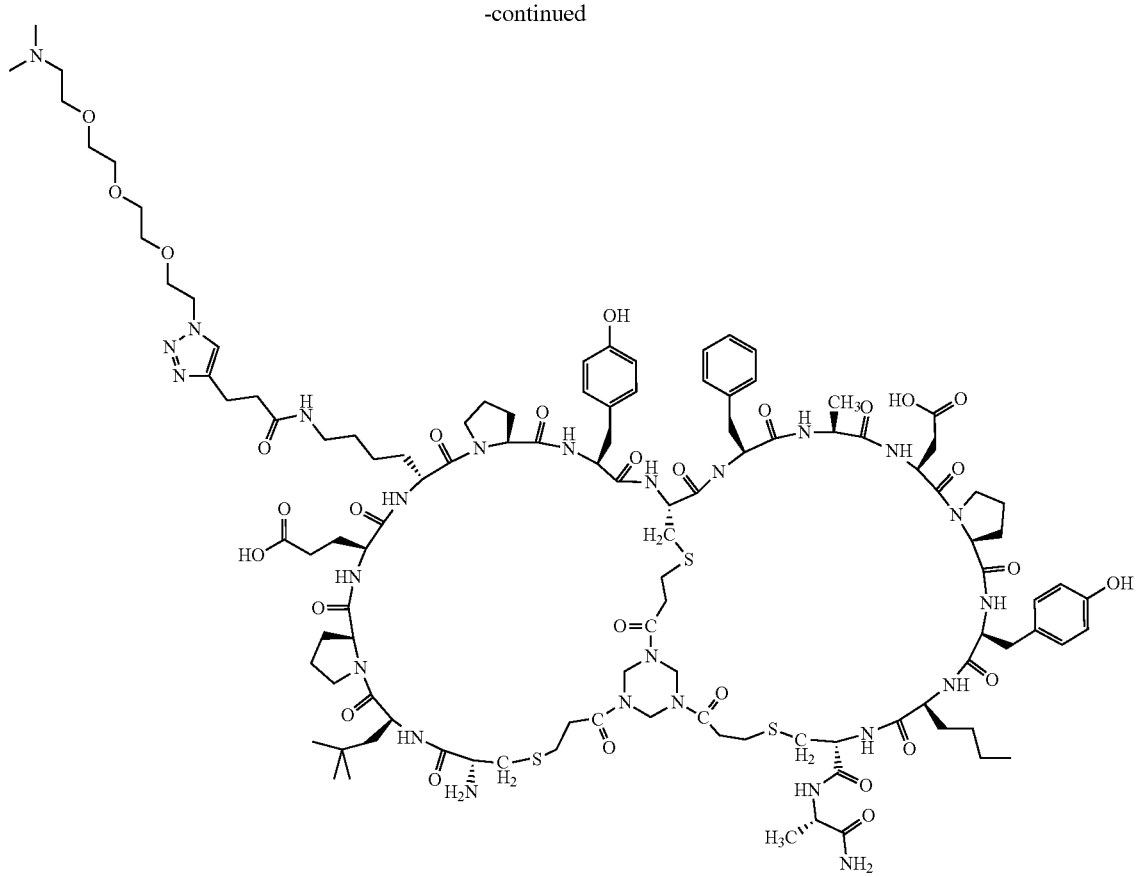
Procedure for Preparation of BCY14602
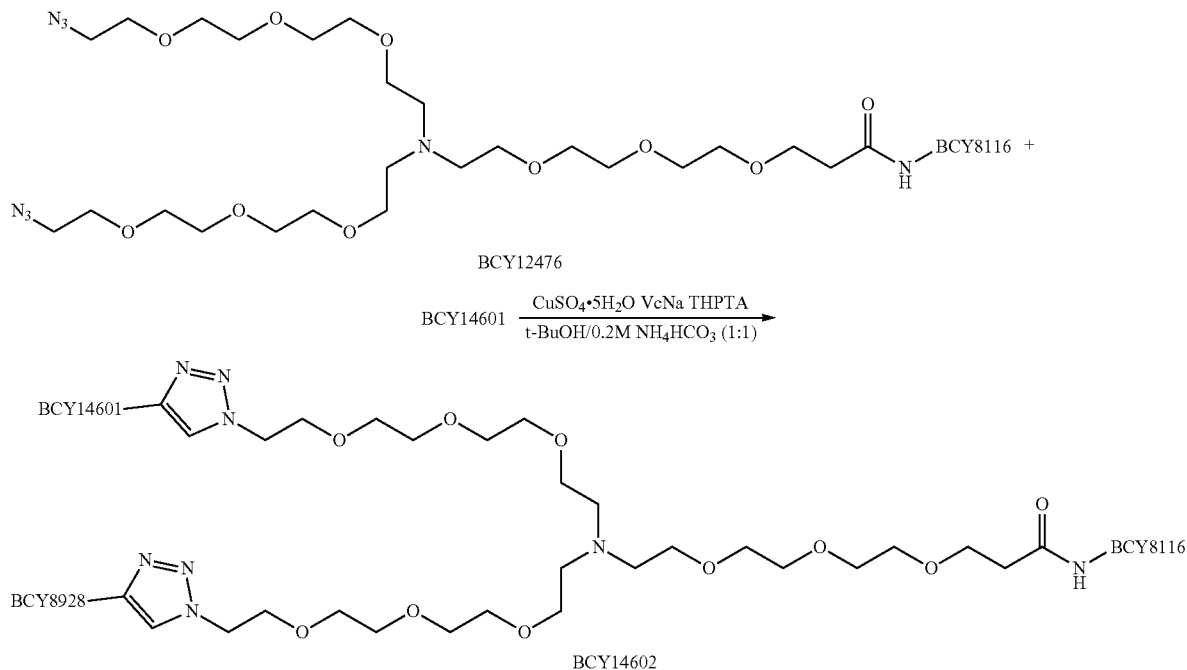

A mixture of BCY12476 (100.0 mg, 36.00 μmol, 1.0 eq), BCY14601 (158.0 mg, 72.63 μmol, 2.04 eq), and THPTA (15.6 mg, 36.00 μmol, 1.0 eq) was dissolved in t-BuOH/0.2 M $NH_4HCO_3$ (1:1, 2 mL, pre-degassed and purged with $N_2$), and then $CuSO_4$ (0.4 M, 89.0 μL, 1.0 eq) and VcNa (28.5 mg, 143.98 μmol, 4.0 eq) were added under $N_2$. The pH of this solution was adjusted to 8, and the solution turned light yellow. THPTA and VcNa were replenished twice, and overall the solution was stirred at 25° C. for 48 hr under $N_2$ atmosphere. LC-MS showed BCY12476 was consumed completely, BCY14601 remained and one main peak with desired m/z was detected. Some byproduct was also detected. The reaction mixture was filtered and concentrated under reduced pressure to give a residue. The crude product was purified by preparative HPLC, and BCY14602 (45.2 mg, 5.51 μmol, 15% yield, 86% purity) was obtained as a white solid. Calculated MW: 7129.2, observed m/z: 1426.6 ($[M+5H]^{5+}$), 1189.1 ($[M+6H]^{6+}$).

Analytical Data

The following heterotandem bicyclic peptide complexes of the invention were analysed using mass spectrometry and HPLC. HPLC setup was as follows:
Mobile Phase: A: 0.1% TFA in $H_2O$ B: 0.1% TFA in ACN
Flow: 1.0 ml/min
Column: Gemini-NX C18 5 um 110A 150*4.6 mm
Instrument: Agilent 1200 HPLC-BE(1-614)

Gradients used are 30-60% B over 20 minutes and the data was generated as follows:

| Complex ID | Analytical Data-Mass Spectrometry | HPLC Retention Time (min) |
|---|---|---|
| BCY11863 | MW: 7213.32, observed m/z: 1444.0 ([M/5+H]+) | 10.649 |

Biological Data

1. CD137 Reporter Assay Co-Culture with Tumor Cells

Culture medium, referred to as R1 media, is prepared by adding 1% FBS to RPMI-1640 (component of Promega kit CS196005). Serial dilutions of test articles in R1 are prepared in a sterile 96 well-plate. Add 25 μL per well of test articles or R1 (as a background control) to designated wells in a white cell culture plate. Tumor cells* are harvested and resuspended at a concentration of 400,000 cells/mL in R1 media. Twenty five (25) μL/well of tumor cells are added to the white cell culture plate. Jurkat cells (Promega kit CS196005, 0.5 mL) are thawed in the water bath and then added to 5 ml pre-warmed R1 media. Twenty five (25) μL/well of Jurkat cells are then added to the white cell culture plate. Incubate the cells and test articles for 6 h at 37° C., 5% $CO_2$. At the end of 6 h, add 75 μL/well Bio-Glo™ reagent (Promega) and incubate for 10 min before reading luminescence in a plate reader (Clariostar, BMG). The fold change relative to cells alone (Jurkat cells+Cell line used in co-culture) is calculated and plotted in GraphPad Prism as log(agonist) vs response to determine $EC_{50}$ (nM) and Fold Induction over background (Max).

The tumor cell type used in co-culture is NCI-H292, CT26 #7, MC38 #13, HT1376, NCI-H322 and T47D which has been shown to express Nectin-4.

Data presented in FIG. 1A shows that the Nectin-4/CD137 heterotandem (BCY11863) induces strong CD137 activation in a CD137 reporter assay and the activation is dependent on the binding of the heterotandem to CD137. BCY11617, a molecule in which CD137 bicyclic peptide is comprised of all D-amino acids which abrogates binding does not induce CD137 agonism.

A summary of the $EC_{50}$ (nM) induced by heterotandem bicyclic peptide complexes BCY11863 and close analogues in a CD137 reporter assay in co-culture with a Nectin-4-expressing tumor cell line is reported in Table 1 below and visualized in FIG. 1B. This data demonstrates the potential of BCY11863 to induce CD137 agonism in coculture with cell lines that have a range of Nectin-4 expression.

TABLE 1

EC50 (nM) of Fold induction over background induced by Nectin-4/CD137 heterotandem bicyclic peptide complexes in a C0137 reporter assay

| Complex ID | Tumor cell line Species | Cell Line used in Coculture | Arithmetic mean $EC_{50}$ (nM) |
|---|---|---|---|
| BCY11863 | mouse | CT26#07 | 0.14 ± 0.07 |
| BCY11863 | mouse | MC38#13 | 0.31 ± 0.26 |
| BCY11863 | human | NCI-H292 | 0.28 ± 0.20 |
| BCY11863 | human | HT1376 | 0.52 ± 0.30 |
| BCY11863 | human | NCI-H322 | 0.33 ± 0.21 |
| BCY11863 | human | T47D | 0.42 ± 0.24 |
| BCY11863 | human | MDA-MB-468 | 0.23 ± 0.01 |
| BCY13582 | human | HT1376 | 0.58 ± 0.27 |
| BCY13582 | human | MDA-MB-468 | 0.34 ± 0.02 |
| BCY13583 | human | HT1376 | 1.7 ± 0.9 |
| BCY13583 | human | MDA-MB-468 | 0.84 ± 0.07 |

2. Human PBMC Co-Culture (Cytokine Release) Assay

Human and mouse tumor cell lines were cultured according to suppliers' recommendations. Frozen PBMCs from healthy human donors were thawed and washed one time in room temperature PBS, and then resuspended in R10 medium. 100 μl of PBMCs (1,000,000 PBMCs/ml) and 100 μl of tumor cells (100,000 tumor cells/ml) (Effector: Target cell ratio (E:T) 10:1) were plated in each well of a 96 well flat bottom plate for the co-culture assay. 100 ng/ml of soluble anti-CD3 mAb (clone OKT3) was added to the culture on day 0 to stimulate human PBMCs. Test, control compounds, or vehicle controls were diluted in R10 media and 50 μL was added to respective wells to bring the final volume per well to 250 μL. Plates were covered with a breathable film and incubated in a humidified chamber at 37° C. with 5% $CO_2$ for three days. Supernatants were collected 48 hours after stimulation, and human IL-2 and IFNγ were detected by Luminex. Briefly, the standards and samples were added to black 96 well plate. Microparticle cocktail (provided in Luminex kit, R&D Systems) was added and shaken for 2 hours at room temperature. The plate was washed 3 times using magnetic holder. Biotin cocktail was then added to the plate and shaken for 1 hour at RT. The plate was washed 3 times using magnetic holder. Streptavidin cocktail was added to the plate and shaken for 30 minutes at RT. The plates were washed 3 times using magnetic holder, resuspended in 100 μL of wash buffer, shaken for 2 minutes at RT, and read using the Luminex 2000. Raw data were analyzed using built-in Luminex software to generate standard curves and interpolate protein concentrations, all other data analyses and graphing were performed using Excel and Prism software. Data represents studies with 3-5 independent donor PBMCs tested in technical triplicates.

Data presented in FIGS. 2A and 2B demonstrate that the Nectin-4/CD137 heterotandem (BCY11863) induces robust IL-2 and IFN-γ cytokine secretion in a PBMC-4T1 co-culture assay. BCY11617 is a negative control that binds Nectin-4 but does not bind CD137.

A summary of the $EC_{50}$ (nM) and maximum IFN-γ cytokine secretion (pg/ml) induced by selected Nectin-4/CD137 heterotandem bicyclic peptide complexes in Human PBMC co-culture (cytokine release) assay is reported in Table 2 below and visualized in FIG. 2C. This demonstrates the potential of BCY11863 to induce cytokine secretion in the presence of a number of different tumor cell lines expressing Nectin-4.

TABLE 2

$EC_{50}$ of IFN-γ cytokine secretion induced by selected Nectin-4/CD137 heterotandem bicyclic peptide complexes in Human PBMC-4T1 co-culture (cytokine release) assay

| Cell Line | IL-2 (nM) | IFNγ (nM) | No. of Donors |
| --- | --- | --- | --- |
| MC38 #13 (mouse) | 0.25 ± 0.08 | 0.17 ± 0.11 | 4 |
| 4T1-D02 (mouse) | 0.16 ± 0.22 | 0.04 ± 0.04 | 4 |
| HT1376 (human) | 0.39 ± 0.29 | 0.23 ± 0.15 | 5 |
| T-47D (human) | 0.20 ± 0.07 | 0.08 ± 0.06 | 3 |
| H322 (human) | 0.84 ± 0.15 | 0.85 ± 0.66 | 3 |
| BCY11863 | 4T1-Parental(Nectin4-) | No induction up to 100 nM | |

3. Pharmacokinetics of the Nectin-4/CD137 Heterotandem BCY11863 in SD Rats

Male SD Rats were dosed with the Nectin-4/CD137 heterotandem BCY11863 formulated in 25 mM Histidine HCl, 10% sucrose pH 7 by IV bolus, IV infusion (15 minutes) or subcutaneously. Serial bleeding (about 80 μL blood/time point) was performed via submandibular or saphenous vein at each time point. All blood samples were immediately transferred into prechilled microcentrifuge tubes containing 2 μL K2-EDTA (0.5M) as anti-coagulant and placed on wet ice. Blood samples were immediately processed for plasma by centrifugation at approximately 4° C., 3000 g. The precipitate including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 μL of the supernatant samples were directly injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T½, AUC(0-last), AUC(0-inf), MRT(0-last), MRT(0-inf) and graphs of plasma concentration versus time profile were reported. The pharmacokinetic parameters from the experiment are as shown in Table 3:

TABLE 3

Pharmacokinetic Parameters in SD Rats

| Compound | Dose (mg/kg) | Dosing Route | T½ (h) | Vdss (L/kg) | Clp (ml/min/kg) | % F |
| --- | --- | --- | --- | --- | --- | --- |
| BCY11863 | 1.9 | IV Bolus | 4.1 | 1.6 | 7.7 | — |
| | 3.2 | IV Inf (15 min) | 3.1 | 1.3 | 9.3 | — |
| | 6.3 | Sc | 2.5 | — | — | 95% |

Data in Table 3 above and FIG. 5 shows that BCY11863 is a low clearance molecule with volume of distribution larger than plasma volume. In addition, the bioavailability from SC dosing of BCY11863 is high in rats.

TABLE 4

Pharmacokinetic Parameters of BCY11863 and potential metabolites in SD Rat PK study following 100 mg/kg dose administered by IV administration

| Analytes | Cmax (ng/mL) | AUC (ng · h/mL) | T1/2 (h) | Vdss (L/kg) | Clp (ml/min/kg) |
| --- | --- | --- | --- | --- | --- |
| BCY11863 | 279540 | 129863 | 5.4 | 2.3 | 13 |
| BCY15155 | 2854 | 1296 | 3.1 | — | — |
| BCY14602 | — | — | — | — | — |

Figure 14:
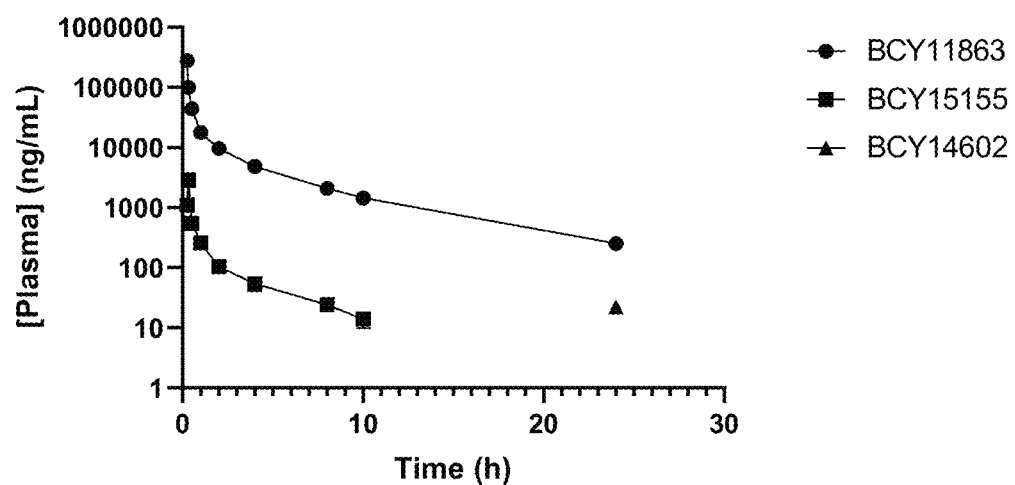
FIG. 14: Pharmacokinetics of heterotandem bicyclic peptide complex BCY11863 in SD Rats dosed IV at 100 mg/kg (n=3) and measurement of concentration of BCY11863 and potential metabolites BCY15155 and BCY14602 in plasma.

Data in Table 4 and FIG. 14 shows that <1% of BCY11863 gets metabolized to BCY15155 upon IV administration of BCY11863 to SD rats. No significant conversion to BCY14602 is noted during the first 24 h of the study.

4. Pharmacokinetics of the Nectin-4/CD137 Heterotandem BCY11863 in Cynomolgus Monkey Non-naïve Cynomolgus Monkeys were dosed via intravenous infusion (15 or 30 min) into the cephalic vein with 1 mg/kg of the Nectin-4/CD137 heterotandem BCY11863 formulated in 25 mM Histidine HCl, 10% sucrose pH 7. Serial bleeding (about 1.2 ml blood/time point) was performed from a peripheral vessel from restrained, non-sedated animals at each time point into a commercially available tube containing potassium (K2) $EDTA*2H_2O$ (0.85-1.15 mg) on wet ice and processed for plasma. Samples were centrifuged (3,000×g for 10 minutes at 2 to 8° C.) immediately after collection. 0.1 mL plasma was transferred into labelled polypropylene micro-centrifuge tubes. 5-fold of the precipitant including internal standard 100 ng/mL Labetalol & 100 ng/mL dexamethasone & 100 ng/mL tolbutamide & 100 ng/mL Verapamil & 100 ng/mL Glyburide & 100 ng/mL Celecoxib in MeOH was immediately added into the plasma, mixed well and centrifuged at 12,000 rpm for 10 minutes at 2 to 8° C. Samples of supernatant were transferred into the pre-labeled polypropylene microcentrifuge tubes, and frozen over dry ice. The samples were stored at −60° C. or below until LC-MS/MS analysis. An aliquot of 40 μL calibration standard, quality control, single blank and double blank samples were added to the 1.5 mL tube. Each sample (except the double blank) was quenched with 200 μL IS1 respectively (double blank sample was quenched with 200 μL MeOH with 0.5% tritonX-100), and then the mixture was vortex-mixed well (at least 15 s) with vortexer and centrifuged for 15 min at 12000 g, 4° C. A 10 μL supernatant was injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T %, AUC(0-last), AUC(0-inf), MRT(0-last), MRT(0-inf) and graphs of plasma concentration versus time profile were reported. The pharmacokinetic parameters for two bispecific compounds are as shown in Table 5.

TABLE 5

Pharmacokinetic Parameters in cynomolgous monkey

| Compound | Dose (mg/kg) | Route | $T_{1/2}$ (h) | Clp (ml/min/kg) | Vdss (L/kg) |
| --- | --- | --- | --- | --- | --- |
| BCY11863 | 0.93 | IV infusion (30 min) | 5.3 | 3.3 | 0.62 |
| | 0.97 | IV infusion (15 min) | 4.5 | 4.8 | 0.91 |
| | 9.4 | IV infusion (15 min) | 8.9 | 3.9 | 1.1 |

Figure 3:
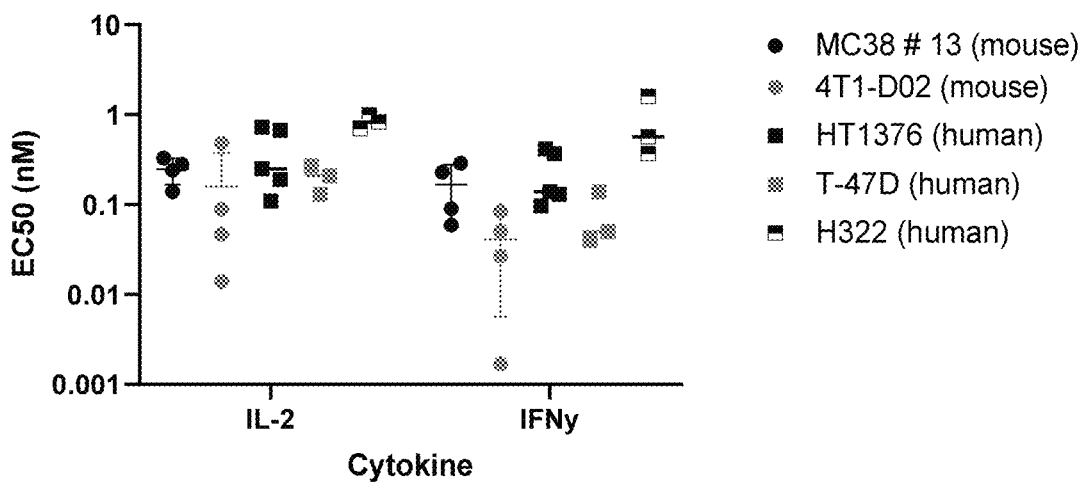
FIG. 3: Pharmacokinetics of heterotandem bicyclic peptide complex BCY11863 in SD Rats and Cynomolgus monkey (cyno) dosed IV at 2 mg/kg (n=3) and 1 mg/kg (n=2) respectively.
Figure 3:
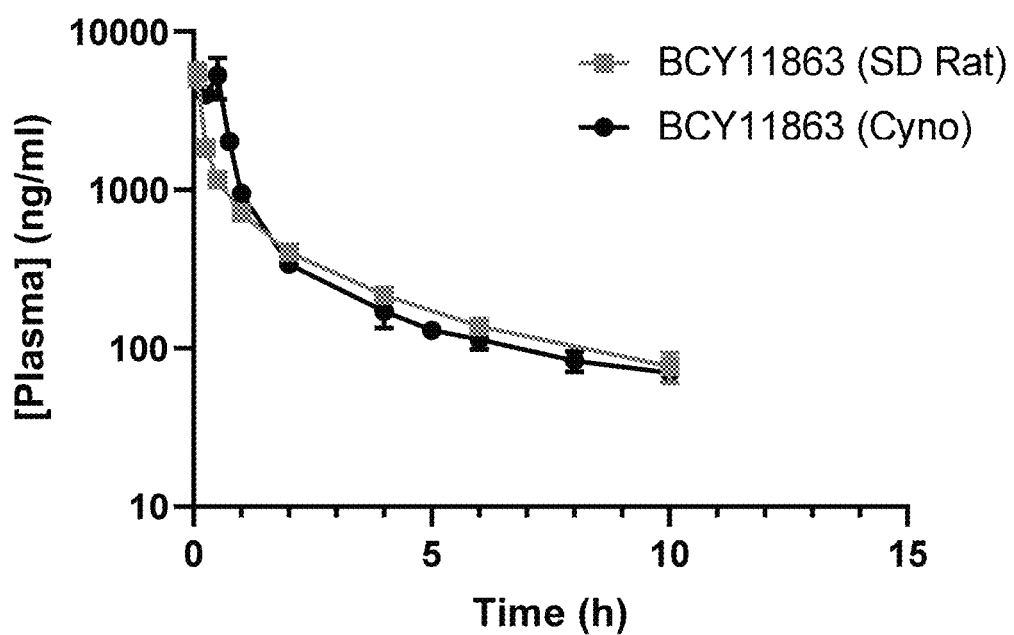

FIG. 3 shows the plasma concentration vs time curve of BCY11863 from a 2 mg/kg IV dose in SD Rat (n=3) and 1 mg/kg IV infusion in cynomolgus monkey (n=2). BCY11863 has a volume of distribution at steady state (Vdss) of 1.6 L/kg and a clearance of 7.7 mL/min/kg in rats which results in a terminal half life of 4.1 h. BCY11863 has a volume of distribution at steady state (Vdss) of 0.62 L/kg and a clearance of 3.3 mL/min/kg in cyno which results in a terminal half life of 5.3 h. Subsequent studies are consistent with these results. The PK parameters from the IV study in cyno indicates that this is a low plasma clearance molecule with volume of distribution similar to total body water.

5. Pharmacokinetics of the Nectin-4/CD137 Heterotandem BCY11863 in CD1 Mice

6 Male CD-1 mice were dosed with 15 mg/kg of the Nectin-4/CD137 heterotandem BCY11863 formulated in 25 mM Histidine HCl, 10% sucrose pH 7 via intraperitoneal or intravenous administration. Serial bleeding (about 80 μL blood/time point) was performed via submandibular or saphenous vein at each time point. All blood samples were immediately transferred into prechilled microcentrifuge tubes containing 2 μL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 μL of the supernatant samples were directly injected for LC-MS/MS analysis using an Orbitrap Q Exactive in positive ion mode to determine the concentrations of analyte. Plasma concentration versus time data were analyzed by non-compartmental approaches using the Phoenix WinNonlin 6.3 software program. C0, CI, Vdss, T½, AUC(0-last), AUC(0-inf), MRT(0-last), MRT(0-inf) and graphs of plasma concentration versus time profile were reported.

Figure 9:
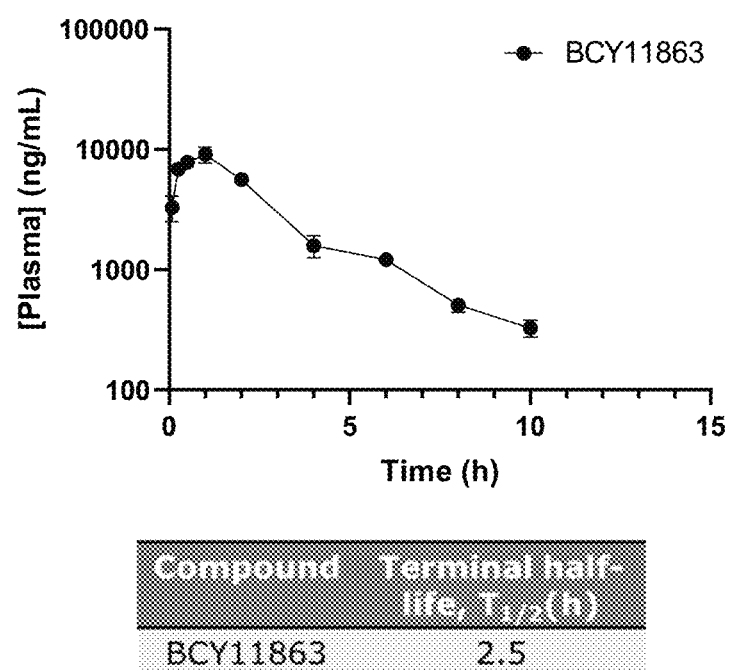
FIG. 9: Plasma concentration vs time curve of BCY11863 from a 15 mg/kg intraperitoneal dose in CD-1 mice (n=3) and the terminal plasma half life for BCY11863.

FIG. 9 shows the plasma concentration vs time curves of BCY11863 from a 15 mg/kg IP dose in CD1 mice (n=3) and the terminal plasma half life for BCY11863.

TABLE 6

Pharmacokinetic Parameters in CD-1 Mice

| Compound | Dose (mg/kg) | Dosing Route | T½ (h) | Vdss (L/kg) | Clp (ml/min/kg) | % F |
|---|---|---|---|---|---|---|
| BCY11863 | 5.6 | IV Bolus | 2.6 | 1.6 | 9.7 | |
| | 0.96 | IV Bolus | 1.7 | 2.9 | 21 | |
| | 12 | IV Bolus | 2.6 | 2.5 | 17 | |
| | 32 | IV Bolus | 2.4 | 2.1 | 16 | |
| | 15.5 | IP | 2.5 | — | — | 100 |

Data in FIG. 9 and Table 6 above shows BCY11863 can be dosed as IV bolus and IP in mice. The bioavailability from IP dosing of BCY11863 is high in mice. The PK parameters from the IV study indicates that this is a low clearance molecule with volume of distribution larger than plasma volume.

6. Anti-Tumor Activity of BCY11863 in a Syngeneic Nectin-4 Overexpressing MC38 Tumor Model (MC38#13)

6-8 weeks old C57BL/6J-hCD137 female mice were inoculated in the flank with $1 \times 10^6$ syngeneic Nectin-4 overexpressing MC38 cells (MC38#13). When tumors reached 72 mm$^3$ size on average, mice were randomized to receive vehicle or BCY11863 (intraperitoneal administration). BCY11863 was administered (n=6 mice/treatment cohort) at either 1 mg/kg or 10 mg/kg either daily (QD) or every three days (Q3D). QD dosed mice received 16 doses of BCY11863 and Q3D dosed mice received 10 doses of BCY11863. Tumor growth was monitored by caliper measurements until day 69 after treatment initiation. The results of this experiment may be seen in FIG. 4 where significant reduction (p<0.05, 2-way ANOVA with Dunnett's test for multiple comparisons) of tumor growth was observed in 2 treatment cohorts by day 7 and by day 14 all treatment groups were significantly different from the vehicle group. By day 48, 22 out of 24 BCY11863-treated animals had responded to the treatment completely and had no palpable tumors remaining.

Based on the circulating plasma half-life of BCY11863 in mice after IP injection (2.5 h), plasma trough levels will be close to 0 after both BCY11863 doses (1 and 10 mg/kg) and dosing intervals (QD and Q3D) thus demonstrating that less than continuous plasma exposure of BCY11863 from intermittent dosing is sufficient to lead to significant anti-tumor activity leading to durable complete responses.

7. BCY11863 Treatment Leads to an Immunogenic Memory to Nectin-4 Overexpressing MC38 Tumor Model On day 69, 5 animals that had responded completely to BCY11863 treatment were re-inoculated with $1 \times 10^6$ MC38#13-cells. A cohort of 5 naïve C57BL/6J-hCD137 female mice were inoculated with $1 \times 10^6$ MC38#13-cells as a control. The results of this experiment may be seen in FIG. 5 where all 5 inoculated naïve C57BL/6J-hCD137 female mice grew tumors by day 13 after inoculation whereas none of the inoculated complete responder mice developed tumors. This demonstrates that animals that achieved a complete antitumor response as a result of BCY11863 treatment have developed immunogenic memory.

8. BCY11863 Demonstrates Anti-Tumor Activity in a Syngeneic Nectin-4 Overexpressing CT26 Tumor Model (CT26#7)

6-8 weeks old BALB/c-hCD137 female mice were inoculated in the flank with $3 \times 10^5$ syngeneic Nectin-4 overexpressing CT26 cells (CT26#7). When tumors reached around 70 mm$^3$ size on average, mice were randomized to receive vehicle or 5 mg/kg BCY11863 intraperitoneally every three days (6 doses total). Tumor growth was monitored by caliper measurements until day 14 after treatment initiation. The results of this experiment may be seen in FIG. 6 where BCY11863 treatment significantly (p<0.0001, Student's t-test) reduced the tumor growth from day 7 forward.

Based on the circulating plasma half-life of BCY11863 in mice at IP injection (2.5 h), plasma exposure will not be continuous throughout the dosing period demonstrating that less than continuous plasma exposure of BCY11863 is sufficient to lead to significant anti-tumor activity.

9. Total T Cells and CD8+ T Cells Increase in CT26#7 Tumor Tissue 1 h after the Last (6$^{th}$) Q3D Dose of BCY11863

1 hour after the last vehicle or BCY11863 dose the CD26#7 bearing mice were sacrificed and tumors were harvested, processed for single cell suspensions and stained for flow cytometry analysis for total T cells (CD45+CD3+), CD8+ T cells (CD45+CD3+CD8+), CD4+ T cells (CD45+CD3+CD4+) and regulatory T cells (Tregs; CD45+CD3+CD4+Foxp3+). The results of this experiment may be seen in FIG. 7 where it can be seen that BCY11863 treatment led to significant increase of total T cells (p<0.0001, Student's t-test) and CD8+ T cells (p<0.0001, Student's t-test) as well as to a significant increase in the CD8+ T cell/Treg ratio (p<0.05, Student's t-test).

This demonstrates that treatment with BCY11863 can lead to an increased level of T-cells locally in the tumor tissue after intermittent dosing.

10. Pharmacokinetic Profiles of BCY11863 in Plasma and Tumor Tissue of CT26#7 Syngeneic Tumor Bearing Animals after a Single Intravenous (iv) Administration of 5 mg/kg of BCY11863

6-8 weeks old BALB/c female mice were inoculated in the flank with $3 \times 10^5$ syngeneic Nectin-4 overexpressing CT26 cells (CT26#7). When tumors reached around 400 mm$^3$ size on average, mice were randomized to receive a single intravenous dose of vehicle or 5 mg/kg BCY11863. A cohort of mice (n=3/timepoint) were sacrificed at 0.25, 0.5, 1, 2, 4, 8 and 24 h timepoints and harvested plasma and tumor tissue were analyzed for BCY11863. For tumor BCY11863 content analysis, tumor homogenate was prepared by homogenizing tumor tissue with 10 volumes (w:v) of homogenizing solution (MeOH/15 mM PBS (1:2, v:v)). 40 μL of sample was quenched with 200 μL IS1 and the mixture was mixed by vortexing for 10 min at 800 rpm and centrifuged for 15 min at 3220 g at 4° C. The supernatant was transfer to another clean 96-well plate and centrifuged for 5 min at 3220 g at 4° C., and 10.0 μL of supernatant was then injected for LC-MS/MS analysis using an Orbitrap Q Exactive in positive ion mode to determine the concentrations of analyte. For plasma BCY11863 content analysis, blood samples were collected in K2-EDTA tubes and immediately processed to plasma by centrifugation at approximately 4° C., 3000 g. 40 μL of plasma sample was quenched with 200 μL IS1 and the mixture was mixed by vortexing for 10 min at 800 rpm and centrifuged for 15 min at 3220 g at 4° C. The supernatant was transferred to another clean 96-well plate and centrifuged for 5 min at 3220 g at 4° C., and 10.0 μL of supernatant was then injected for LC-MS/MS analysis using an Orbitrap Q Exactive in positive ion mode to determine the concentrations of analyte.

Figure 8:
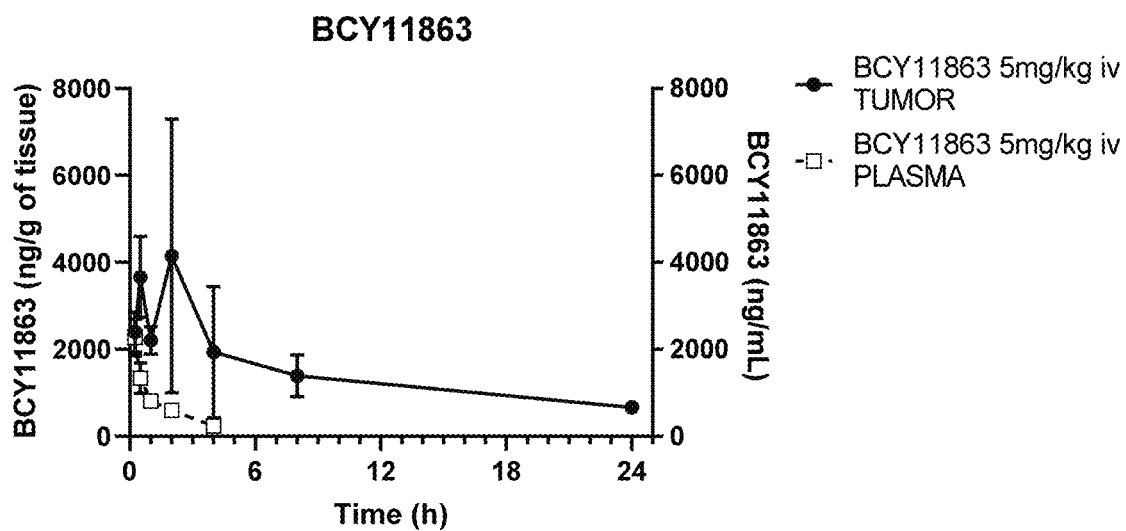
FIG. 8: Pharmacokinetic profiles of BCY11863 in plasma and tumor tissue of CT26#7 syngeneic tumor bearing animals after a single intravenous (iv) administration of 5 mg/kg of BCY11863.

The results of this experiment are shown in FIG. 8 where it can be seen that BCY11863 was retained in the tumor tissue after the plasma BCY11863 is eliminated from circulation as indicated by the difference of BCY11863 plasma $T_{1/2}$ (1.65 h) and tumor $T_{1/2}$ (13.4 h).

11. Binding of BCY11863 to Nectin-4 and CD137 Across Four Preclinical Species

The binding of BCY11863 to its primary target Nectin-4 and CD137 was characterized using surface plasmon resonance (SPR).

(a) Nectin-4

BCY11863 binds to cyno, rat, mouse and human Nectin-4 with $K_D$ between 5-27 nM as measured by direct binding to the extracellular domain that has been biotinylated and captured on a streptavidin sensor chip surface.

TABLE 7

Binding affinities of BCY11863 to Biotinylated-Nectin-4 extracellular domain: SPR data

| SPR $K_D$ (nM) | Assay Type | Human (25° C.) | Human (37° C.) | NHP (25° C.) | Rat (25° C.) | Mouse (25° C.) |
|---|---|---|---|---|---|---|
| BCY11863 | Direct Binding | 5.0 ± 2.1 n = 7 | 5.2 ± 1.1 n = 9 | 27 ±15 n = 9 | 15 ± 1 n = 6 | 4.6 ± 2.1 n = 9 |

To understand whether the binding of BCY11863 to Nectin-4 was altered in the context of the ternary complex, i.e. when also bound to CD137, a multicomponent SPR binding assay was developed. BCY11863 was first captured to human CD137 immobilized on the SPR chip surface and then Nectin-4 from different species were passed over the chip to determine their affinities to the captured BCY11863 (see FIG. 10C). The affinities to Nectin-4 were generally maintained in the presence of CD137 binding as shown below:

TABLE 8

Binding affinities of BCY11863 to Nectin-4 extracellular domain using biotinylated human CD137 as capture reagent

| SPR $K_D$ (nM) | Assay Type | Human | NHP | Rat | Mouse |
|---|---|---|---|---|---|
| BCY11863 | Sandwich Assay | 12 ± 2 n = 4 | 28 ± 5 n = 3 | 25 ± 2 n = 3 | 6.7 ± 1.7 n = 3 |

(b) CD137

Direct binding of BCY11863 to surface bound CD137 cannot be measured accurately by SPR because of avidity resulting from two CD137 binding bicycles in BCY11863 which leads to extremely slow $k_{off}$ (See FIG. 10B). In addition, biotinylation of cyno CD137 abrogates binding of BCY11863, likely due to modification of a lysine on the cyno protein that is important for BCY11863 binding. Hence, a BCY11863 analogue containing a C-terminal biotinylated lysine (BCY13582) was tested in SPR to determine cross species specificity of BCY11863. BCY13582 was captured to the sensor chip using a reversible biotin capture kit and the affinities to Nectin-4 from different species were determined. Both strategies showed that these BCY11863 analogs bound to human and cyno CD137 with $K_D$<10 nM and had negligible binding to both mouse and rat CD137.

TABLE 9

Binding affinities of biotinylated BCY11863 analogues to CD137 extracellular domain: SPR data

| SPR $K_D$ (nM) | Assay Type | Human | NHP | Rat | Mouse |
|---|---|---|---|---|---|
| BCY13582 | Direct Binding | 8.4 ± 4.2 n = 3 | 4.23 n = 1 | NB n = 1 | NB n = 1 |

To understand whether the binding of BCY11863 to CD137 was altered in the context of the ternary complex, i.e. when also bound to Nectin-4, a dual binding SPR binding assay was developed. BCY11863 was first captured to human Nectin-4 immobilized on the SPR chip surface and then soluble CD137 from different species were passed over the chip to determine their affinities to the captured BCY11863 (see FIG. 10D). The affinities to CD137 were generally maintained in the presence of Nectin-4 binding as shown below:

TABLE 10

Binding affinities of BCY11863 to CD137 ECD using biotinylated human Nectin-4 as capture reagent

| SPR $K_D$ (nM) | Assay Type | Human | NHP | Rat | Mouse |
|---|---|---|---|---|---|
| BCY11863 | Dual Binding | 6.3 ± 0.7 n = 4 | 18 ± 6 n = 3 | NB n = 2 | NB n = 2 |

FIG. 10A shows one example sensorgram which demonstrates that BCY11863 binds to Nectin-4 (human) with an affinity of 4.1 nM. FIG. 10B shows the sensorgram that BCY11863 binds to CD137 (human) with high affinity. Due to the presence of 2 CD137 binding bicycles in BCY11863, the off rate from immobilized CD137 protein is very slow and the reported $K_D$ may be an overestimation (FIG. 10B). FIG. 10C shows BCY11863 binds to Nectin-4 while the CD137 arms are bound to CD137 protein immobilized on the chip to form a ternary complex. FIG. 10D shows BCY11863 binds to CD137 while the Nectin-4 binding arm is bound to Nectin-4 protein immobilized on the chip to form a ternary complex. FIG. 10E demonstrates the ability of BCY13582 immobilized on SPR chip to bind human CD137.

12. Selectivity of BCY11863 for Nectin-4 and CD137

Nectin-4 Paralogue screening: Binding of BCY11863 was assessed using SPR against Nectin-1 (2880-N1, R&D Systems), Nectin-2 (2229-N2, R&D Systems), Nectin-3 (3064-N3, R&D Systems), Nectin-like-1 (3678-S4-050, R&D Systems), Nectin-like-2 (3519-S4-050, R&D Systems), Nectin-like-3 (4290-S4-050, R&D Systems), Nectin-like-4 (4164-S4, R&D Systems) and Nectin-like-5 (2530-CD-050, R&D Systems) by labelling them with biotin and immobilizing them on a streptavidin surface. BCY11863 did not show any binding to these targets up to a concentration of 5000 nM.

CD137 Paralogue screening: Binding of streptavidin captured BCY13582 (biotinylated-BCY11863) was assessed using SPR against soluble TNF family receptors OX40 and CD40. BCY13582 did not bind to these targets up to a concentration of 100 nM.

Retrogenix microarray screening: Retrogenix's cell microarray technology was used to screen for specific off-target binding interactions of a biotinylated BCY11863 known as BCY13582.

Investigation of the levels of binding of the test peptide to fixed, untransfected HEK293 cells, and to cells over-expressing Nectin-4 and CD137 (TNFRSF9), showed 1 µM of the test peptide to be a suitable screening concentration. Under these conditions, the test peptide was screened for binding against human HEK293 cells, individually expressing 5484 full-length human plasma membrane proteins and secreted proteins. This revealed 9 primary hits, including Nectin-4 and CD137.

Each primary hit was re-expressed, along with two control receptors (TGFBR2 and EGFR), and re-tested with 1 µM BCY13582 test peptide, 1 µM BCY13582 test peptide in the presence of 100 µM BCY11863, and other positive and negative control treatments (FIG. 4). After removing non-specific, non-reproducible and non-significant hits, there remained three specific interactions for the test peptide. These were untethered and tethered forms of Nectin-4, and CD137—the primary targets.

No specific off-target interactions were identified for BCY13582, indicating high specificity for its primary targets.

13. Anti-Tumor Activity of BCY11863 in a Syngeneic Nectin-4 Overexpressinq MC38 Tumor Model (MC38#13) on Dosing on Twice a Week at 5 mg/kg at 0.24 h and 10 mg/kg at 0 h 6-8 week old female C57BL/6J-hCD137 mice [B-hTNFRSF9(CD137) mice; Biocytogen] were implanted subcutaneously with 1×10⁶ MC38#13 (MC38 cells engineered to overexpress murine Nectin-4) cells. Mice were randomized into treatment groups (n=6/cohort) when average tumor volumes reached around 95 mm³ and were treated with a weekly dose of vehicle (25 mM histidine, 10% sucrose, pH7) or 10 mg/kg BCY11863 with two different dosing schedules for two dosing cycles (5 mg/kg BCY11863 at 0 h and 24 h on D0 and D7, or 10 mg/kg at 0 h on D0 and D7). All treatments were administered intravenously (IV). Tumor growth was monitored until Day 15 from treatment initiation.

BCY11863 leads to significant anti-tumor activity with both dosing schedules, but the dose schedule with 5 mg/kg dosing at 0 h and 24 h was superior to 10 mg/kg dosing at 0 h when complete responses were analyzed on day 15 after treatment initiation (FIG. 12). 5 mg/kg BCY11863 at 0 h and 24 h on D0 and D7 dosing led to 4 out of 6 complete tumor responses whereas 10 mg/kg BCY11863 at 0 h on D0 and D7 dosing led to one out of 6 complete tumor responses. These data together with the BCY11863 mouse plasma PK data indicate that maintaining a BCY11863 plasma exposure at the level produced by 5 mg/kg 0 h and 24 h dosing in a weekly cycle produces close to complete anti-tumor response in the MC38#13 tumor model.

14. Anti-Tumor Activity of BCY11863 in a Syngeneic Nectin-4 Overexpressing MC38 Tumor Model (MC38#13)

At 3 weekly doses of 3, 10 and 30 mg/kg with dose fractionated weekly, biweekly and daily 6-8 week old female C57BL/6J-hCD137 mice [B-hTNFRSF9(CD137) mice; Biocytogen] were implanted subcutaneously with 1×10⁶ MC38#13 (MC38 cells engineered to overexpress murine Nectin-4) cells. Mice were randomized into treatment groups (n=6/cohort) when average tumor volumes reached around 107 mm³ and were treated with 21 daily doses of vehicle (25 mM histidine, 10% sucrose, pH7). BCY11863 treatment was done at three different total dose levels (3, 10 and 30 mg/kg total weekly dose) fractionated in three different schedules (QD: daily; BIW: twice a week or QW: weekly). Different BCY11863 treatment cohorts received either 21 daily doses (0.43, 1.4 or 4.3 mg/kg), 6 twice weekly doses (1.5, 5 or 15 mg/kg) or 3 weekly doses (3, 10 or 30 mg/kg). All treatments were administered intravenously (IV). Tumor growth was monitored until tumor reached volumes over 2000 mm³ or until 31 days after treatment initiation. Complete responders (animals with no palpable tumors) were followed until D52.

BCY11863 leads to significant anti-tumor activity with many of the dosing schedules the BIW dosing schedule being the most efficacious schedule, the 5 mg/kg BIW dose in particular. This is demonstrated by the number of complete responder animals on day 52. On day 52 after treatment initiation, 15/18 mice treated BIW with BCY11863 were complete responders, 12/18 mice treated QD with BCY11863 were complete responders and 6/18 mice treated QW with BCY11863 were complete responders. 5 mg/kg BIW dosing lead to 100% complete response rate with 6/6 CRs (FIG. 13). These data together with the BCY11863 mouse plasma PK data indicate that continuous BCY11863 plasma exposure is not needed for anti-tumor response to BCY11863 in the MC38#13 tumor model.

The invention claimed is:

1. A heterotandem bicyclic peptide complex comprising:

(a) a first peptide ligand which binds to Nectin-4 and which has the sequence $C_i$P[1Nal][dD]$C_{ii}$M[HArg]DWSTP[HyP]W$C_{iii}$ (SEQ ID NO: 1); conjugated via an N-(acid-$PEG_3$)-N-bis($PEG_3$-azide) linker to (b) two second peptide ligands which bind to CD137 both of which have the sequence Ac-$C_i$[tBuAla]PE[D-Lys(PYA)]PY$C_{ii}$FADPY[Nle]$C_{iii}$-A (SEQ ID NO: 2);

or a pharmaceutically acceptable salt thereof, wherein each of said peptide ligands comprise a polypeptide comprising three reactive cysteine groups ($C_i$, $C_{ii}$ and $C_{iii}$), separated by two loop sequences, and a molecular scaffold which is 1,1',1"-(1,3,5-triazinane-1,3,5-triyl)triprop-2-en-1-one (TATA) and which forms covalent bonds with the reactive cysteine groups of the polypeptide such that two polypeptide loops are formed on the molecular scaffold;

wherein Ac represents acetyl, HArg represents homoarginine, HyP represents trans-4-hydroxy-L-proline, 1Nal represents 1-naphthylalanine, tBuAla represents t-butyl-alanine, PYA represents 4-pentynoic acid and Nle represents norleucine.

2. The heterotandem bicyclic peptide complex according to claim 1 which is:

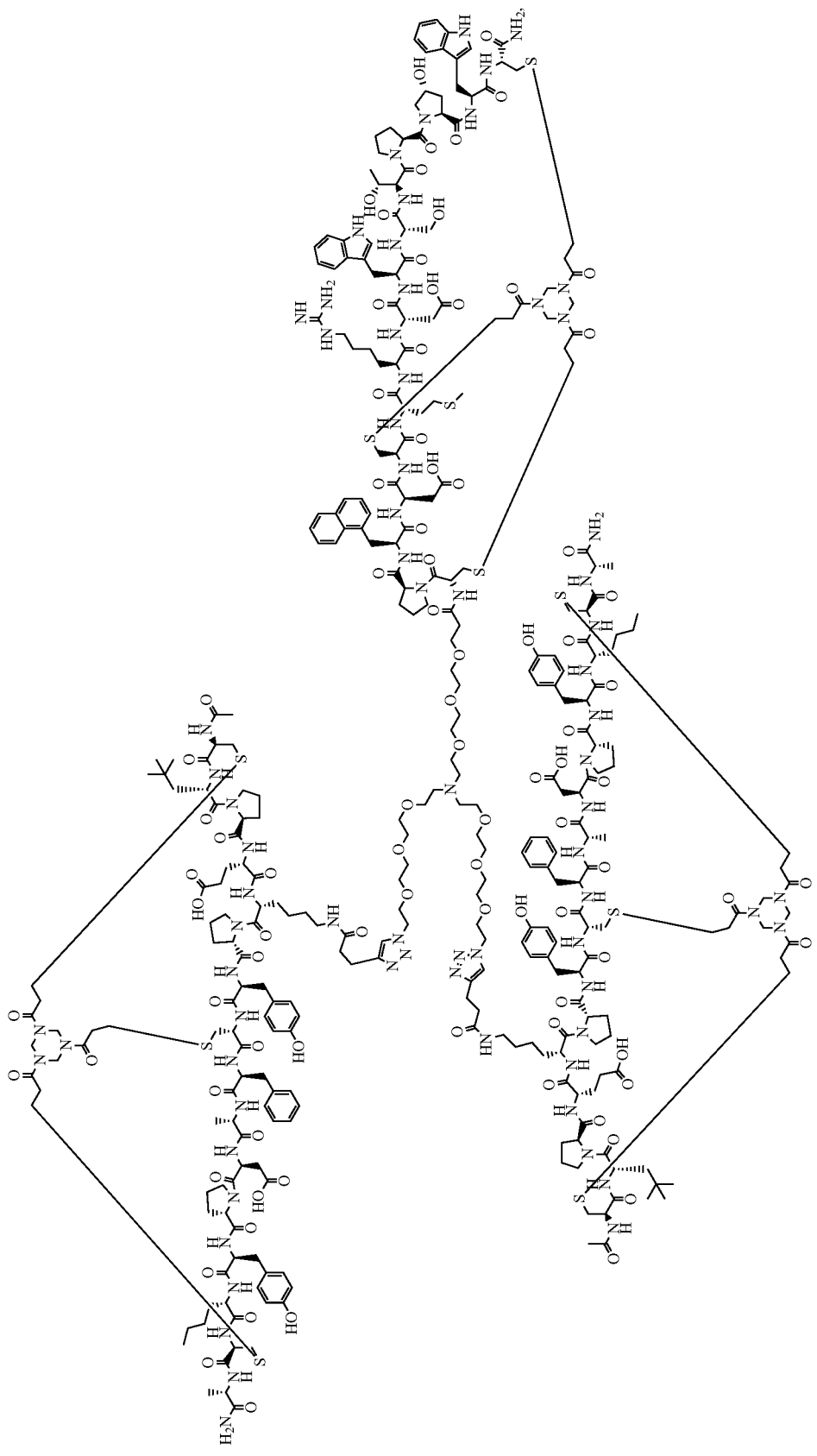

or a pharmaceutically acceptable salt thereof.

3. The heterotandem bicyclic peptide complex as defined in claim 1, wherein the pharmaceutically acceptable salt is selected from the free acid or the sodium, potassium, calcium, or ammonium salt.

4. A pharmaceutical composition which comprises the heterotandem bicyclic peptide complex of claim 1, or a pharmaceutically acceptable salt thereof, in combination with one or more pharmaceutically acceptable excipients.

5. A method of preventing, suppressing or treating cancer, comprising administering the heterotandem bicyclic peptide complex as defined in claim 1, or a pharmaceutically acceptable salt thereof.

6. The method of claim 5, wherein the cancer is lung cancer, colon cancer, bladder cancer, or breast cancer.

7. A method of treating cancer which comprises administration of the heterotandem bicyclic peptide complex as defined in claim 1, or a pharmaceutically acceptable salt thereof, at a dosage frequency which does not sustain plasma concentrations of said complex above the in vitro $EC_{50}$ of said complex.

8. The method of claim 7, wherein the cancer is lung cancer, colon cancer, bladder cancer, or breast cancer.

9. The method of claim 7, wherein the dosage frequency is once per week.

10. The method of claim 7, wherein the dosage frequency is twice per week.

11. A heterotandem bicyclic peptide complex which is:

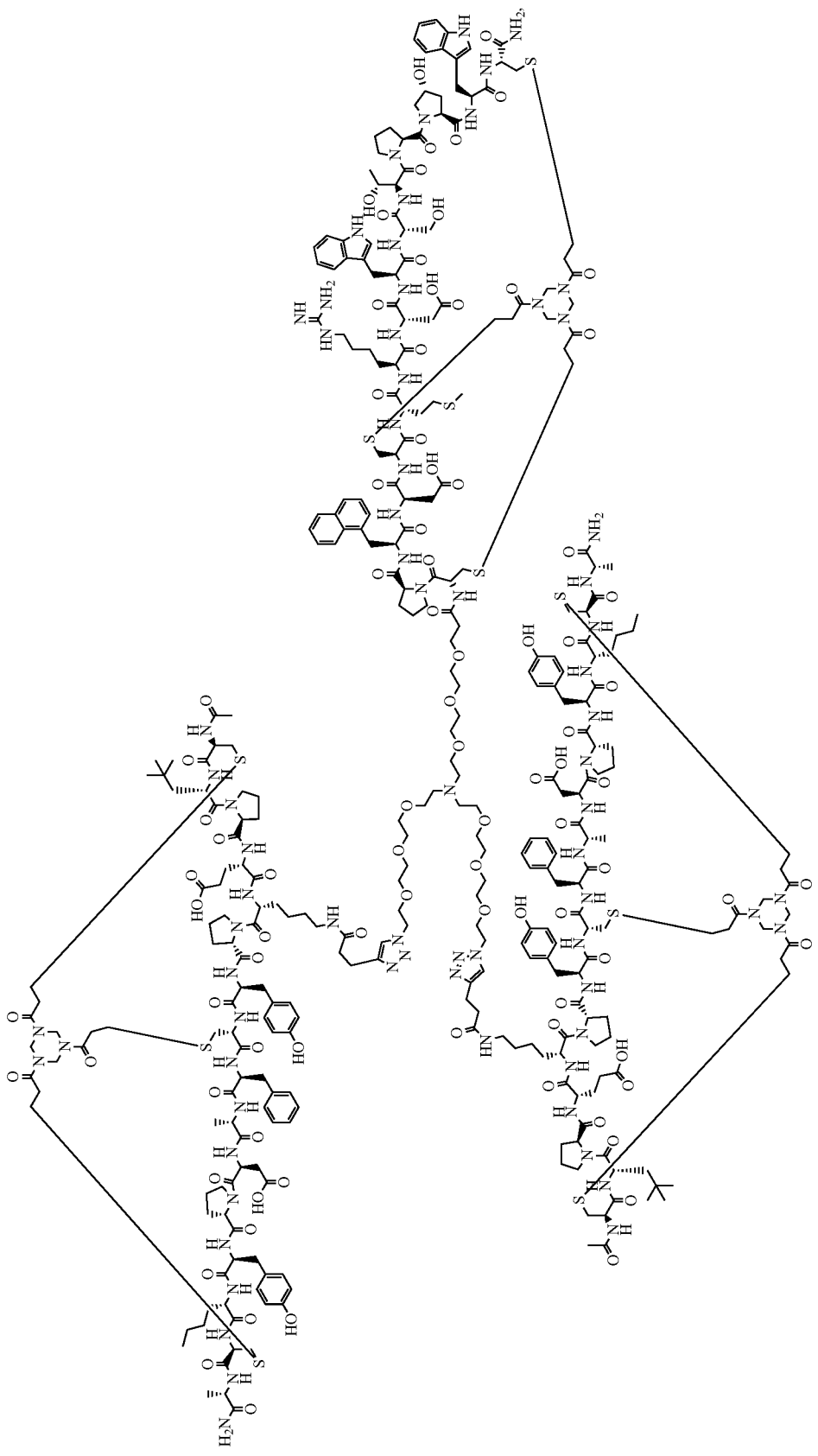

or a pharmaceutically acceptable salt thereof.

12. The heterotandem bicyclic peptide complex of claim 11, wherein the pharmaceutically acceptable salt is selected from the free acid or the sodium, potassium, calcium, or ammonium salt.

13. A pharmaceutical composition comprising the heterotandem bicyclic peptide complex of claim 11, or a pharmaceutically acceptable salt thereof, in combination with one or more pharmaceutically acceptable excipients.

14. A method of preventing, suppressing or treating cancer, comprising administering the heterotandem bicyclic peptide complex of claim 11, or a pharmaceutically acceptable salt thereof.

15. The method of claim 14, wherein the cancer is lung cancer, colon cancer, bladder cancer, or breast cancer.

16. A method of treating cancer which comprises administration of the heterotandem bicyclic peptide complex of claim 11, or a pharmaceutically acceptable salt thereof, at a dosage frequency which does not sustain plasma concentrations of said complex above the in vitro $EC_{50}$ of said complex.

17. The method of claim 16, wherein the cancer is lung cancer, colon cancer, bladder cancer, or breast cancer.

18. The method of claim 16, wherein the dosage frequency is once per week.

19. The method of claim 16, wherein the dosage frequency is twice per week.

* * * * *

SEQUENCE LISTING

<160> NUMBER OF SEQ ID NOS: 4

<210> SEQ ID NO 1

```
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 1

Cys Pro Xaa Asp Cys Met Xaa Asp Trp Ser Thr Pro Xaa Trp Cys
1               5                   10                  15

<210> SEQ ID NO 2
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 2

Cys Xaa Pro Glu Xaa Pro Tyr Cys Phe Ala Asp Pro Tyr Xaa Cys Ala
1               5                   10                  15

<210> SEQ ID NO 3
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 3

Cys Xaa Pro Glu Xaa Pro Tyr Cys Phe Ala Asp Pro Tyr Xaa Cys Ala
1               5                   10                  15

<210> SEQ ID NO 4
<211> LENGTH: 16
<212> TYPE: PRT
<213> ORGANISM: Artificial
<220> FEATURE:
```

-continued

```
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 4

Cys Xaa Pro Glu Xaa Pro Tyr Cys Phe Ala Asp Pro Tyr Xaa Cys Lys
1               5                   10                  15
```